US009332939B2

(12) United States Patent
Osorio

(10) Patent No.: US 9,332,939 B2
(45) Date of Patent: *May 10, 2016

(54) DETECTING, QUANTIFYING, AND/OR CLASSIFYING SEIZURES USING MULTIMODAL DATA

(71) Applicant: Flint Hills Scientific, L.L.C., Lawrence, KS (US)

(72) Inventor: Ivan Osorio, Leawood, KS (US)

(\*) Notice: Subject to any disclaimer, the term of this patent is extended or adjusted under 35 U.S.C. 154(b) by 0 days.

This patent is subject to a terminal disclaimer.

(21) Appl. No.: 14/543,734

(22) Filed: Nov. 17, 2014

(65) Prior Publication Data

US 2015/0073237 A1 Mar. 12, 2015

Related U.S. Application Data

(63) Continuation of application No. 13/692,738, filed on Dec. 3, 2012, now Pat. No. 8,888,702, which is a continuation of application No. 12/896,525, filed on Oct. 1, 2010, now Pat. No. 8,337,404.

(51) Int. Cl.
| | |
|---|---|
| *A61B 5/00* | (2006.01) |
| *A61B 5/025* | (2006.01) |
| *A61B 5/11* | (2006.01) |
| *A61B 5/0205* | (2006.01) |
| *A61B 5/0476* | (2006.01) |
| *A61B 5/0245* | (2006.01) |
| *A61B 5/145* | (2006.01) |
| *A61B 3/113* | (2006.01) |
| *A61B 5/0468* | (2006.01) |
| *A61B 5/0472* | (2006.01) |
| *A61B 5/0488* | (2006.01) |
| *A61B 5/16* | (2006.01) |
| *A61B 7/00* | (2006.01) |
| *A61N 1/36* | (2006.01) |
| *A61N 1/365* | (2006.01) |
| *A61B 5/024* | (2006.01) |
| *A61B 5/053* | (2006.01) |
| *A61B 5/08* | (2006.01) |

(52) U.S. Cl.
CPC ............... *A61B 5/4094* (2013.01); *A61B 3/113* (2013.01); *A61B 5/0205* (2013.01); *A61B 5/0245* (2013.01); *A61B 5/0468* (2013.01); *A61B 5/0472* (2013.01); *A61B 5/0476* (2013.01); *A61B 5/0488* (2013.01); *A61B 5/11* (2013.01); *A61B 5/1117* (2013.01); *A61B 5/14539* (2013.01); *A61B 5/14542* (2013.01); *A61B 5/165* (2013.01); *A61B 5/7264* (2013.01); *A61B 5/7282* (2013.01); *A61B 7/003* (2013.01); *A61B 5/02055* (2013.01); *A61B 5/02405* (2013.01); *A61B 5/0531* (2013.01); *A61B 5/08* (2013.01); *A61B 5/686* (2013.01); *A61N 1/36064* (2013.01); *A61N 1/36135* (2013.01); *A61N 1/36585* (2013.01)

(58) Field of Classification Search
None
See application file for complete search history.

(56) References Cited

U.S. PATENT DOCUMENTS

| | | | | |
|---|---|---|---|---|
| 5,928,272 | A * | 7/1999 | Adkins et al. | ............ 607/45 |
| 7,979,130 | B2 * | 7/2011 | Carlson et al. | ............ 607/45 |

(Continued)

*Primary Examiner* — Brian T Gedeon

(57) ABSTRACT

Methods, systems, and apparatus for detecting an epileptic event, for example, a seizure in a patient using a medical device. The determination is performed by providing an autonomic signal indicative of the patient's autonomic activity; providing a neurologic signal indicative of the patient's neurological activity; and detecting an epileptic event based upon the autonomic signal and the neurologic signal.

23 Claims, 11 Drawing Sheets

(56) References Cited

U.S. PATENT DOCUMENTS 8,135,473 B2 * 3/2012 Miesel et al. .................. 607/49
2007/0118054 A1 * 5/2007 Pinhas et al. .................. 600/587
2011/0251468 A1 * 10/2011 Osorio .......................... 600/300
2011/0270346 A1 * 11/2011 Frei et al. ........................ 607/45

* cited by examiner

Not to scale

DETECTING, QUANTIFYING, AND/OR CLASSIFYING SEIZURES USING MULTIMODAL DATA

CROSS-REFERENCE TO RELATED APPLICATIONS

This application is a continuation application of co-pending U.S. application Ser. No. 13/692,738 filed Dec. 3, 2012, which is a continuation of U.S. patent application Ser. No. 12/896,525, filed Oct. 1, 2010, now U.S. Pat. No. 8,337,404, which issued on Dec. 25, 2012. Both Ser. Nos. 13/692,738 and 12/896,525 are incorporated by reference herein.

FIELD OF THE INVENTION

This invention relates to medical device systems and methods capable of detecting and, in some embodiments, treating an occurring or impending seizure using multimodal data.

DESCRIPTION OF THE RELATED ART

Of the approximately 60 million people worldwide affected with epilepsy, roughly 23 million people suffer from epilepsy resistant to multiple medications. In the USA alone, the annual cost of epilepsy care is USD 12 billion (in 1995 dollars), most of which is attributable to subjects with pharmaco-resistant seizures. Pharmaco-resistant seizures are associated with an increase mortality and morbidity (e.g., compared to the general population and to epileptics whose seizures are controlled by medications) and with markedly degraded quality of life for patients. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present invention is a signal applied from a medical device, e.g., a neurostimulator.

A "therapeutic signal" refers to a stimulation signal delivered to a patient's body with the intent of treating a medical condition through a suppressing (e.g., blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of the nervous system, stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic seizures) see Osorio et al., Ann Neurol 2005; Osorio & Frei IJNS 2009) The mechanisms thorough which this suppressing effect takes place are described in the foregoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (e.g., wave annihilation) may be exerted through collision with identical, similar or dissimilar waves, a concept borrowed from wave mechanics, or through phase resetting (Winfree).

In some cases, electrotherapy may be provided by implanting an electrical device, i.e., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

While contingent (also referred to as "closed-loop," "active," or "feedback" stimulation (i.e., electrotherapy applied in response to sensed information, such as heart rate) stimulation schemes have been proposed, non-contingent, programmed periodic stimulation is the prevailing modality. For example, vagus nerve stimulation for the treatment of epilepsy usually involves a series of grouped electrical pulses defined by an "on-time" (such as 30 sec.) and an "off-time" (such as 5 min.). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-3.5 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the sum of the on-time and off-time, and which describes the fraction of time that the electrical signal is applied to the nerve.

In VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-300 Hz (i.e., 20 pulses per second to 300 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation-based therapy for this purpose. For example, it may be desirable to detect an occurring or impending seizure. Such detection may be useful in triggering a therapy, monitoring the course of a patient's disease, or the progress of his or her treatment thereof. Alternatively or in addition, such detection may be useful in warning the patient of an impending seizure or alerting the patient, a physician, a caregiver, or a suitably programmed computer in order for that person or computer program to take action intended to reduce the likelihood, duration, or severity of the seizure or impending seizure, or to facilitate further medical treatment or intervention for the patient. In particular, detection of an occurring or impending seizure enables the use of contingent neurostimulation. The state of the art does not provide an efficient and effective means for performing such detection and/or warning. Conventional VNS stimulation as described above does not detect occurring or impending seizures.

Closed-loop neurostimulation therapies for treating epilepsy have been proposed in which stimulation is triggered based upon factors including EEG activity (see, e.g., U.S. Pat. No. 5,995,868 and U.S. Pat. No. 7,280,867) as well as cardiac-based activity (see, e.g., U.S. Pat. No. 6,961,618 and U.S. Pat. No. 5,928,272). EEG- or ECoG-based approaches involving recording of neural electrical activity at any spatio-temporal scale involve determination of one or more parameters from brain electrical activity that indicate a seizure. Such approaches have met with limited success and have a number of drawbacks, including highly invasive and technically demanding and costly surgery for implanted systems, and the poor patient compliance for external systems (which require the patient to wear electrodes on the scalp for extended periods).

SUMMARY OF THE INVENTION

In one embodiment, the present invention provides a method for detecting an epileptic event based upon multimodal signals such as an autonomic signal and a neurologic signal of a patient. In one embodiment, the method comprises providing an autonomic signal indicative of the patient's autonomic activity; providing a neurologic signal indicative of the patient's neurological activity; and detecting an epileptic event based upon the autonomic signal and the neurologic signal.

In one embodiment the autonomic signal is a cardiac signal, and the neurologic signal is a kinetic signal. In another embodiment, a first autonomic signal is a respiratory signal and a second autonomic signal is a dermal signal (e.g., sweat glands). In yet another embodiment, the autonomic signal is a cardiac signal, the neurologic signal is included, and a metabolic signal is included.

In one embodiment, the present invention provides a computer readable program storage device encoded with instructions that, when executed by a computer, performs a method for detecting an epileptic event based upon a patient's cardiac signal and kinetic activity. The method includes: providing a kinetic signal indicative of a body movement of the patient; calculating based on the kinetic signal a kinetic score indicative of a correlation of said kinetic signal with an epileptic event; detecting an epileptic event based upon the patient's heart beat sequence; and providing an output indicative of an epileptic event based on the kinetic score.

In another embodiment, the present invention provides a computer readable program storage device encoded with instructions that, when executed by a computer, performs a method for detecting an epileptic event based upon a patient's cardiac signal and kinetic activity. The method includes: providing a kinetic signal indicative of a body movement of the patient; classifying the kinetic signal as either an epileptic event kinetic signal or a nonepileptic event kinetic signal; detecting an epileptic event based upon changes in the patient's heart beat sequence; confirming the detecting if said kinetic signal is classified as an epileptic event kinetic signal; overriding the detecting if said kinetic signal is classified as a nonepileptic event kinetic signal; and providing an output indicative of an epileptic event only if the detecting is confirmed.

In yet another embodiment, the present invention provides an implantable medical device for detecting an epileptic event based upon an autonomic signal and a neurologic signal of a patient. The implantable medical device includes a detection module for receiving an autonomic signal indicative of the patient's autonomic activity and for receiving a neurologic signal indicative of the patient's neurological activity. The implantable medical device also includes a processing element for determining whether an epileptic event has occurred based upon the autonomic signal and the neurologic signal.

In one embodiment, the present invention provides a method for detecting a primarily or secondarily generalized tonic-clonic seizure based upon two or more of a patient's body signals. In one embodiment, the method comprises providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; an isometric force signal indicative of the patient's muscle activity; a sound signal indicative of the patient's oral utterances or vocalizations; an ocular signal indicative of the patient's eye movement; a responsiveness signal indicative of the patient's responsiveness; an awareness signal indicative of the patient's awareness; and a stress marker signal indicative of at least one stress marker of the patient; and detecting the generalized tonic-clonic epileptic seizure based upon the timewise correlation of two features, one feature being of each of the at least two body signals, wherein the feature of the cardiac signal is an increase in the patient's heart rate above a reference value; the feature of the accelerometer signal is an increase in the patient's movement above a reference value followed by a decrease in the patient's movement below a reference value; the feature of the inclinometer signal is a change of the patient's body position indicative of a fall; the feature of the respiratory signal is a respiration rate outside of an interictal reference range; the feature of the skin resistivity signal is a decrease in the patient's skin resistivity below a reference value; the feature of the blood gas signal is a decrease in the patient's blood oxygen content below a reference value, an increase in carbon dioxide content above a reference value, or both; the feature of the blood pH signal is a decrease in the patient's blood pH below a reference value; the feature of the isometric force signal is an increase in the patient's muscle activity above a reference value; the feature of the sound signal is an increase in the patient's oral utterances or vocalizations indicative of an epileptic cry; the feature of the ocular signal is an increase in the patient's eye movement above a reference value; the feature of the responsiveness signal is a decrease in the patient's responsiveness below a reference value; the feature of the awareness signal is a decrease in the patient's awareness below a reference value; and the feature of the stress marker signal is an increase in at least one stress marker of the patient above a reference value.

In one embodiment, the present invention also provides a computer readable program storage device encoded with instructions that, when executed by a computer, performs a method for detecting a partial epileptic seizure based upon two or more of a patient's body signals. In one embodiment, this method comprises providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; a sound signal indicative of the patient's oral utterances or vocalizations; a responsiveness signal indicative of the patient's responsiveness; an awareness signal indicative of the patient's awareness; and a stress marker signal indicative of at least one stress marker of the patient; and detecting the partial epileptic seizure based upon the timewise correlation of two features, one feature being of each of the at least two body signals, wherein the feature of the cardiac signal is a heart rate outside an interictal reference value range; the feature of the accelerometer signal is a movement velocity outside an interictal reference value range; the feature of the respiratory signal is a respiration rate, tidal volume, minute volume, or pattern outside of an interictal reference value range; the feature of the skin resistivity signal is a skin resistivity outside an interictal reference value range; the feature of the blood gas signal is an increase in the patient's blood oxygen content above an interictal reference value, a decrease in carbon dioxide content below an interictal reference value, or both; the feature of the blood pH signal is a blood pH outside an interictal reference value range; the feature of the sound signal is a change in the pattern, loudness, timbre or quality, semantic content and contextual relevance of the patient's oral utterances or vocalizations compared to utterances or vocalizations to the non-seizure state; and the feature of the stress marker signal is a concentration of at least one stress marker outside an interictal reference value range.

In yet another aspect of the present invention, a computer readable program storage device is provided that is encoded with instructions that, when executed by a computer, perform a method described above.

In one embodiment, a medical device is provided comprising an autonomic signal module, a kinetic signal module, a detection module, and a processor adapted to perform a method as described above.

In yet another aspect of the present invention, a medical device system for detecting an epileptic event based upon multimodal signals, is provided. The medical device system includes a sensor for detecting a first modal data and a second modal data relating to a patient's body. The first modal data includes an autonomic signal and the second modal data includes a neurologic signal of the patient's body. The medical device system also includes an implantable medical device (IMD) operatively coupled to the sensor(s). The implantable medical device includes: a neurologic signal module for receiving the neurologic signal; an autonomic signal module for receiving the autonomic signal; and a processing element for determining whether an epileptic event has occurred based upon the first and second modal data.

BRIEF DESCRIPTION OF THE DRAWINGS

The invention may be understood by reference to the following description taken in conjunction with the accompanying drawings, in which like reference numerals identify like elements, and in which.

Figure 1:
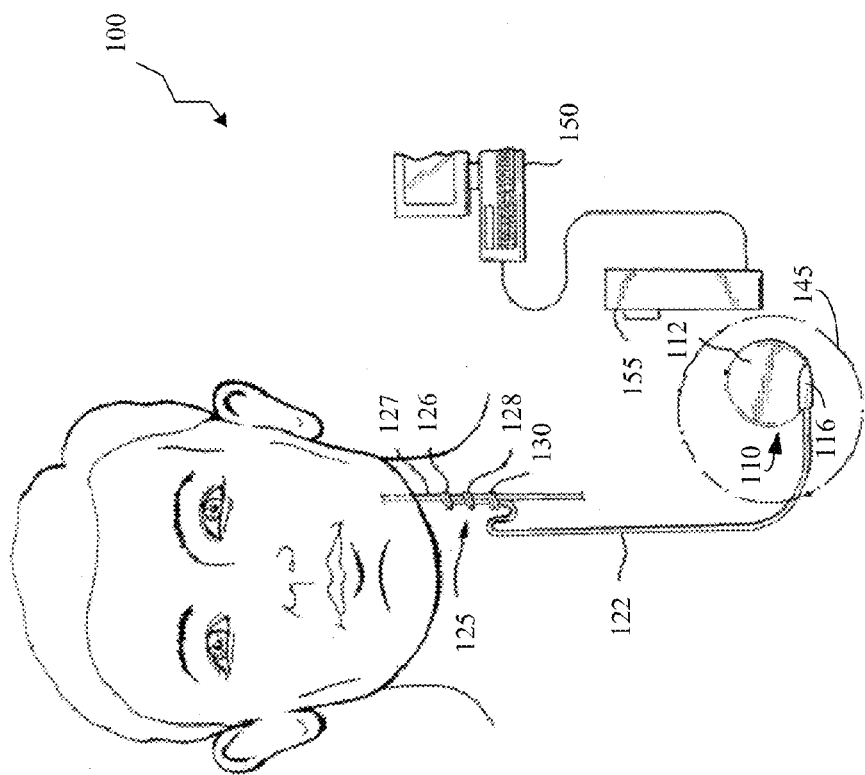
FIG. 1 provides a stylized diagram of a medical device implanted into a patient's body for providing a therapeutic signal to a structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

Identification of changes in brain state (whether physiologic or pathologic) has traditionally been accomplished through analysis of electrical brain signals and behavioral observation. Continuous (e.g., round-the-clock) automated monitoring of changes in brain state imposes certain limitations on the utilization of these traditional methods, due to the difficulties inherent to automated ambulatory video, the large amount of data produced per unit time, and the excessive demands on human and technical resources required to maintain an acceptable signal/noise for electrical signals recorded from the scalp. Additionally, scalp signals have poor temporo-spatial resolution, a characteristic which results in both low sensitivity and specificity of state-of-brain detection changes.

Implanted sensors or electrodes beneath the scalp but above the outer skull table or intracranial (epidural, subdural or depth) have been used to overcome the limitations of scalp recordings. However, although the quality of recordings (especially for intracranial electrodes) is much better (e.g., typically has a higher S/N) than that from scalp electrodes, the quality is still limited and there are risks (e.g., infection, bleeding, brain damage) associated with these devices, not to mention cost and scarcity of neurosurgeons to perform this type of procedures.

While electrical brain signals and behavioral observation may provide information for classification of brain states, this task can be accomplished more efficiently, more precisely, and/or more cost-effectively through monitoring of other biological signals such those generated by the heart, muscle, skin, eyes, tympanic membrane temperature, and body posture/movement, since they may not require surgery, or if surgery is required for implantation, the procedures are much shorter, simpler, and cheaper that those required for recording of brain signals and there is no shortage of human resources. Certain highly valuable neurological signals (e.g., cognitive) for detection, quantification, and classification of state changes may obtained non-invasively and can be used in this invention.

These multi-modal (e.g., autonomic, neurologic, etc) signals can be used individually or in combination to monitor continuously the brain and generate a state-of the-system/organ report, in real-time for the detection, quantification, classification, validation, control and logging of physiologic or pathologic state changes. This approach takes advantage of the inherent and finely tuned dynamical coupling among these systems. For instance, changes in brain state/activity may result in changes in heart activity, muscle activity, and skin properties.

Herein, Applicant describes a method, systems, and devices that may: a) detect in real-time pre-specified changes in brain state; b) quantify their duration, intensity, and time of occurrence; c) classify their type (e.g., epileptic vs. non-epileptic seizures; primarily vs. secondarily generalized seizures; generalized vs. partial seizures; complex vs., simple partial seizures; d) use as a basis for warning and control/therapy, and/or e) save this information to memory for future retrieval for optimization of detection, quantification and classification of state changes and assessment and optimization of therapeutic (e.g., control) efficacy. Non-epileptic movements in this invention refer to those resembling movements seen during tonic-clonic seizures but which are not caused by those seizures.

Herein, "multimodal" refers to epileptic event detection based on more than one endogenous mode or type of signal. The multimodal epileptic event detection disclosed herein provides a comprehensive, cost-effective, valuable alternative to systems of epileptic event detection exclusively based on brain electrical signals such as EEG. To date, no multimodal systems have been developed or commercialized. Multimodal epileptic event detection may make use of signals or markers of autonomic, neurologic, endocrine, metabolic, gastro-intestinal, and/or dermal origin and of tissue/organ stress, such as those presented in Table 1.

Multimodal detection of state changes takes advantage of the fact that certain brain structures directly or indirectly influence autonomic, endocrine, gastro-intestinal, dermal and metabolic functions and that certain abnormal states (e.g. seizures) stress the body tissues and result in the elevation of certain compounds or molecules (e.g., stress markers) that may be used to detect and verify the occurrence of said abnormal state.

It has been established that seizures in humans originating from or spreading to central autonomic structures induce changes in heart rate, among other cardio-vascular indices. It should be stated that seizure-induced heart rate increases (which are far more frequent than heart rate decreases) are not primarily the result of increased motor activity or of metabolic changes, but are instead a neurogenic phenomenon. In the present invention, a highly robust, efficient and reliable system is provided for detecting, quantifying and/or classifiying epileptic seizures based upon multi-modal signals and, if desired, using this information to provide warnings, therapies and optimization of all of these tasks. Systems of the present invention are suitable for commercial, long-term implants or external devices and provide reliable and accurate indications of seizure events for a wide variety of epilepsy patients.

eye signal, a blood signal, and two or more thereof. The autonomic signal can be provided by an electrocardiogram (EKG) device, a pupillometer, a face or body temperature monitor, a skin resistance monitor, a sound sensor, a pressure sensor, a blood gas sensor, among others, or two or more thereof.

Any neurologic signal indicative of the patient's neurological activity can be used in the method. In one embodiment, the neurologic signal is selected from the group consisting of a brain signal, a kinetic signal, and two or more thereof. The neurologic signal can be provided by an electroencephalography (EEG) device, an electrocorticography (ECoG) device, an accelerometer, an inclinometer, an actigraph, a responsiveness testing device or system, among others, or two or more thereof.

TABLE 1

Multimodal Signals

Autonomic

Cardiac: EKG, PKG, Echocardiography, Apexcardiography (ApKG), Intra-cardiac pressure, Cardiac blood flow, cardiac thermography; from which can be derived, e.g., heart rate (HR), change of HR, rate of change of HR, heart rate variability (HRV), change of HRV, rate of change of HRV, HRV vs. HR. Also, blood pressure, heart sounds, heart rhythm, heartbeat wave morphology, heartbeat complex morphology, and thoracic wall deflection.
Vascular: Arterial Pressure, Arterial and venous blood wave pressure morphology; Arterial and venous blood flow velocity, arterial and venous blood flow sounds, arterial and venous thermography
Respiratory: Frequency, tidal volume, minute volume, respiratory wave morphology, respiratory sounds, end-tidal CO2, Intercostal EMG, Diaphragmatic EMG, chest wall and abdominal wall motion, from which can be derived, e.g.,, respiration rate (RR), change of RR, rate of change of RR. Also, arterial gas concentrations, including oxygen saturation, as well as blood pH can be considered respiratory signals.
Dermal: Skin resistance, skin temperature, skin blood flow, sweat gland activity
Concentrations of catecholamines (and their metabolites) and acetylcholine or acetylcholinesterase activity in blood, saliva and other body fluids concentrations and its rate of change.
Neurologic Cognitive/behavioral: Level of consciousness, attention, reaction time, memory, visuo-spatial, language, reasoning, judgment, mathematical calculations, auditory and/or visual discrimination
Kinetic: Direction, speed/acceleration, trajectory (1D to 3D), pattern, and quality of movements, force of contraction, body posture, body orientation/position, body part orientation/position in reference to each other and to imaginary axes, muscle tone, agonist-to-antagonist muscle tone relation, from which can be derived, e.g., information about gait, posture, accessory movements, falls
Vocalizations: Formed, unformed
EEG/ECoG, Evoked potentials, field potentials, single unit activity
Endocrine: Prolactin, luteinizing hormone, follicle stimulation hormone, growth hormone, ACTH, cortisol, vasopressin, beta-endorphin, beta, lipotropin-, corticotropin-releasing factor (CRF)
Stress Markers: Reactive oxygen and nitrogen species including but not limited to iso- and neuro-prostanes and nitrite/nitrate ratio, gluthathione, gluthatione disulfide and gluthatione peroxidase activity, citrulline, protein carbonyls, thiobarbituric acid, the heat shock protein family, catecholamines, lactic acid, N-acetylaspartate, and metabolites of any of the foregoing.
Metabolic: arterial pH and gases, lactate/pyruvate ratio, electrolytes, glucose In one embodiment, the present invention relates to a method for detecting an epileptic event based upon an autonomic signal (e.g., a cardiac signal) and a neurologic signal (e.g., a kinetic signal) of a patient, comprising providing an autonomic signal indicative of the patient's autonomic activity; providing a neurologic signal indicative of the patient's neurological activity; detecting an epileptic event based upon the autonomic signal and the neurologic signal.

"Epileptic event" refers to a seizure, a period of increased likelihood of a seizure, a pre-ictal period, or a post-ictal period, among others.

Any autonomic signal indicative of the patient's autonomic activity can be used in the method. In one embodiment, the autonomic signal is selected from the group consisting of a cardiac signal, a respiratory signal, a skin resistivity signal, an An epileptic event can be detected based upon the autonomic signal and the neurologic signal. The partial basis upon the autonomic signal can make use of techniques described in other patents or patent applications, such as U.S. Pat. Nos. 5,928,272; 7,643,881; U.S. patent application Ser. No. 12/770,562, which are hereby incorporated herein by reference. The partial basis upon the neurologic signal can make use of techniques described in other patents or patent applications, such as U.S. Pat. No. 7,630,757, which are hereby incorporated herein by reference.

In one embodiment, when the autonomic signal is a cardiac signal, the detection can be partially based on the observation that some seizure types are associated with a change (e.g., increase) in heart rate compared to a reference heart rate value range, such as a range of measures of central tendency of heart rate over a short or relatively long time window. Some other seizure types are associated with a decrease in heart rate above a reference heart rate value (see for example, FIG. 4).

Generally, when the term "reference value" is used herein without further qualification, it refers to a value derived from an interictal period. Reference values or ranges thereof for any of the autonomic, neurologic, endocrine, metabolic or stress marker features are day of time (e.g., circadian) and state (e.g., resting wakefulness) dependent and thus non-stationary. Although reference values for a certain feature in a certain state or time are most directly comparable to corresponding signals in the same state or time, they may be comparable to corresponding signals from other states, times, or both.

As used in FIGS. 4-7, clinical onset refers to the earlier of either a) when a patient notices a first seizure symptom, or b) when an expert observer (or a person familiar with the patient's seizures) observes a first change indicative of the seizure. It must be underscored that while the most apparent change may be the "first" to be noticed by the patient or seen by the observer, this change may have been preceded by other (unnoticed or unobserved) changes, and that the "first change" defining the seizure onset may not be the first change actually occurring and associated with the seizure. Only one of several indicia or signs of a seizure may be clinically recognizable, and the clinical onset time is thus given or determined by this clinically recognizable sign or symptom. This does not preclude other clinical symptoms having occurred prior to the clinically recognizable sign or symptom. This is illustrated, for example, in FIG. 6, in which the onset of impaired responsiveness precedes, by a few seconds, the clinical onset, and where the EKG and respiratory changes are also shown as occurring before clinical onset.

Figure 4:
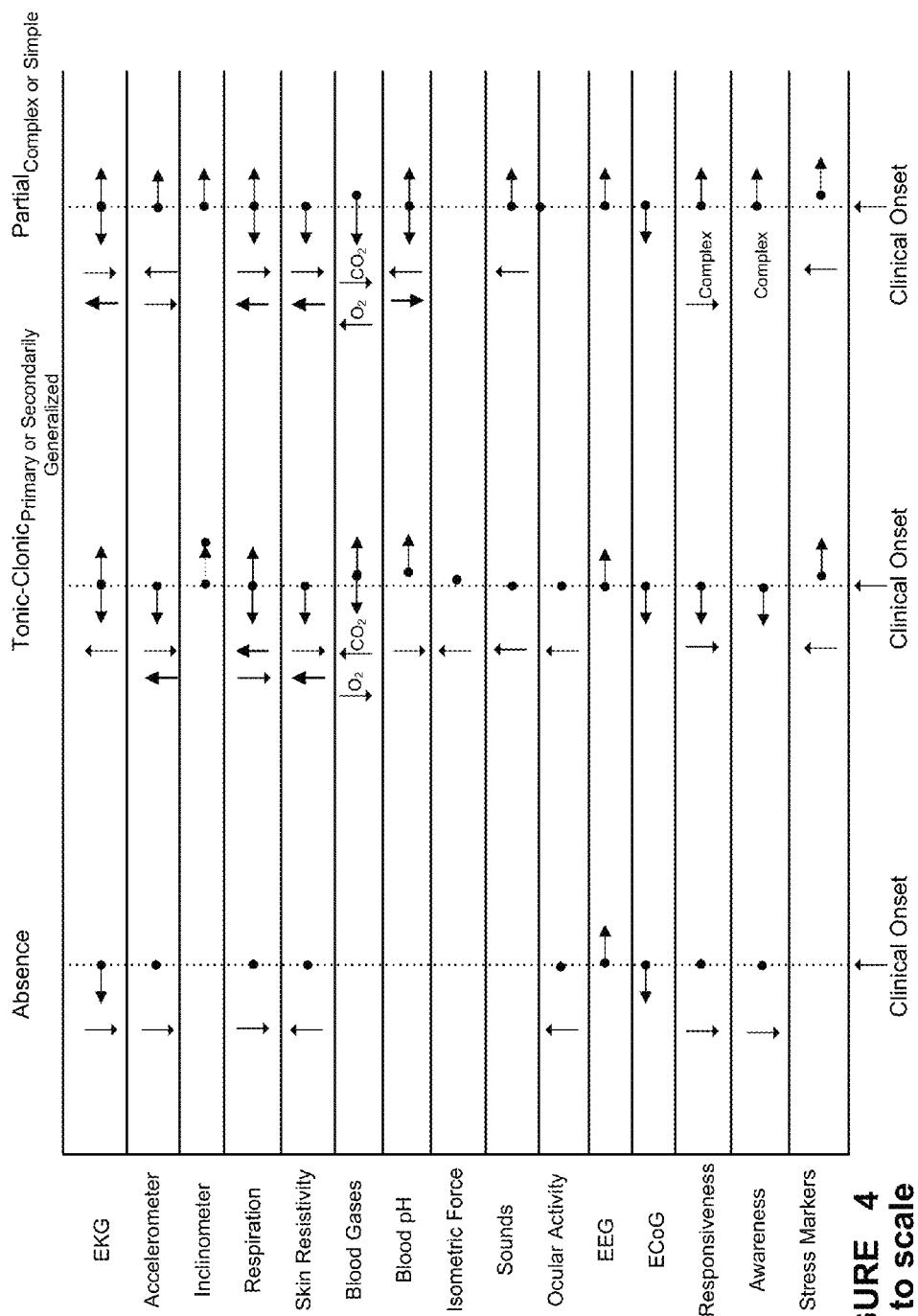
FIG. 4 shows the time of appearance (relative to clinical onset, dashed vertical line) and direction of deviations from reference activity of a plurality of body signals for four seizure types, specifically, absence seizures, tonic-clonic seizures, and simple or complex partial seizures.

FIG. 4 shows the time of appearance (relative to clinical onset, dashed vertical line) and direction of deviations from interictal reference activity, of a plurality of body signals for four seizure types: specifically, absence seizures, generalized tonic-clonic seizures (whether primarily or secondarily generalized), and simple or complex partial seizures. The horizontal arrows show the times of appearance of the symptom change in reference to clinical onset as defined in the present application. A dot without horizontal arrows indicates that the most important aspect of the signal change occurs at clinical onset. This does not exclude the possibility that this change may reappear or change direction at some later time. Upward vertical arrows indicate an increase in the value of the signal while downwards arrows indicate a decrease in value. Arrow length does not reflect a scale or magnitude of the change. When multiple deviations are shown, the larger, thicker arrow is the one most commonly seen over general patient populations. Of course, the skilled epileptologist is aware that some patients will show one or more variations from the typical cases shown in FIG. 4.

To facilitate understanding, certain important details about certain body signals, their onset, and temporal evolution in reference to clinical onset (dashed lines) have been omitted from FIGS. 4-7. These figures should be viewed only as illustrative of the changes in body signals that occur with the various seizure classes.

Figure 5:
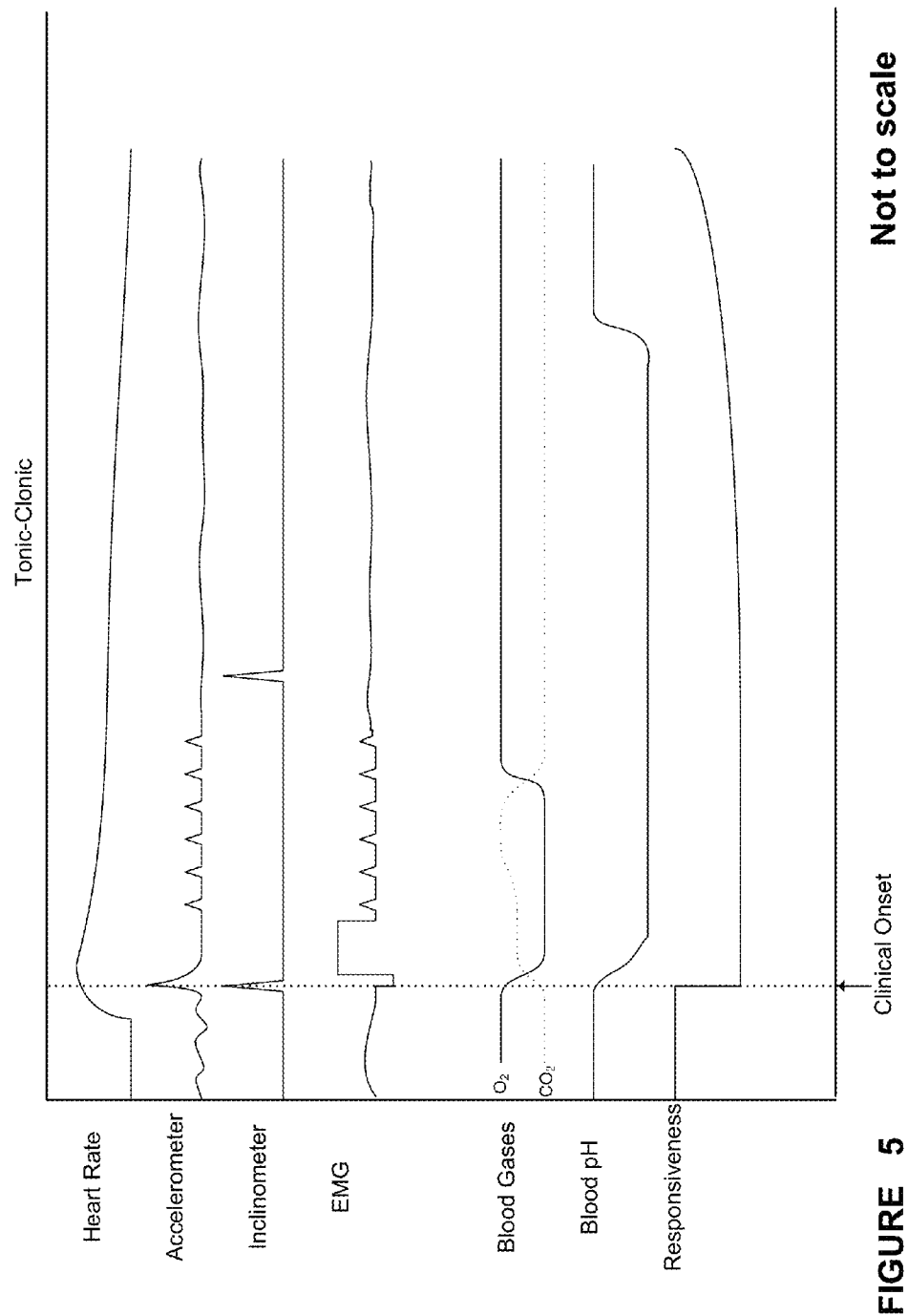
FIG. 5 shows time courses (relative to clinical onset, dashed vertical line) of activity of a plurality of body signals for tonic-clonic seizures.

For example, tonic-clonic seizures are often correlated with an increase in heart rate beginning at about seizure onset (see for example, FIG. 5).

For another example, partial seizures are often correlated with an increase in heart rate beginning before, at, or shortly after electrographic seizure onset. The increase is less than that associated with tonic-clonic seizures (see for example, FIG. 6).

In another embodiment, when the autonomic signal is a respiratory signal, the detection can be partially based on the observation that some seizure types are associated with a deviation of the respiration rate from a reference respiration rate value range (see for example, FIG. 4).

Figure 6:
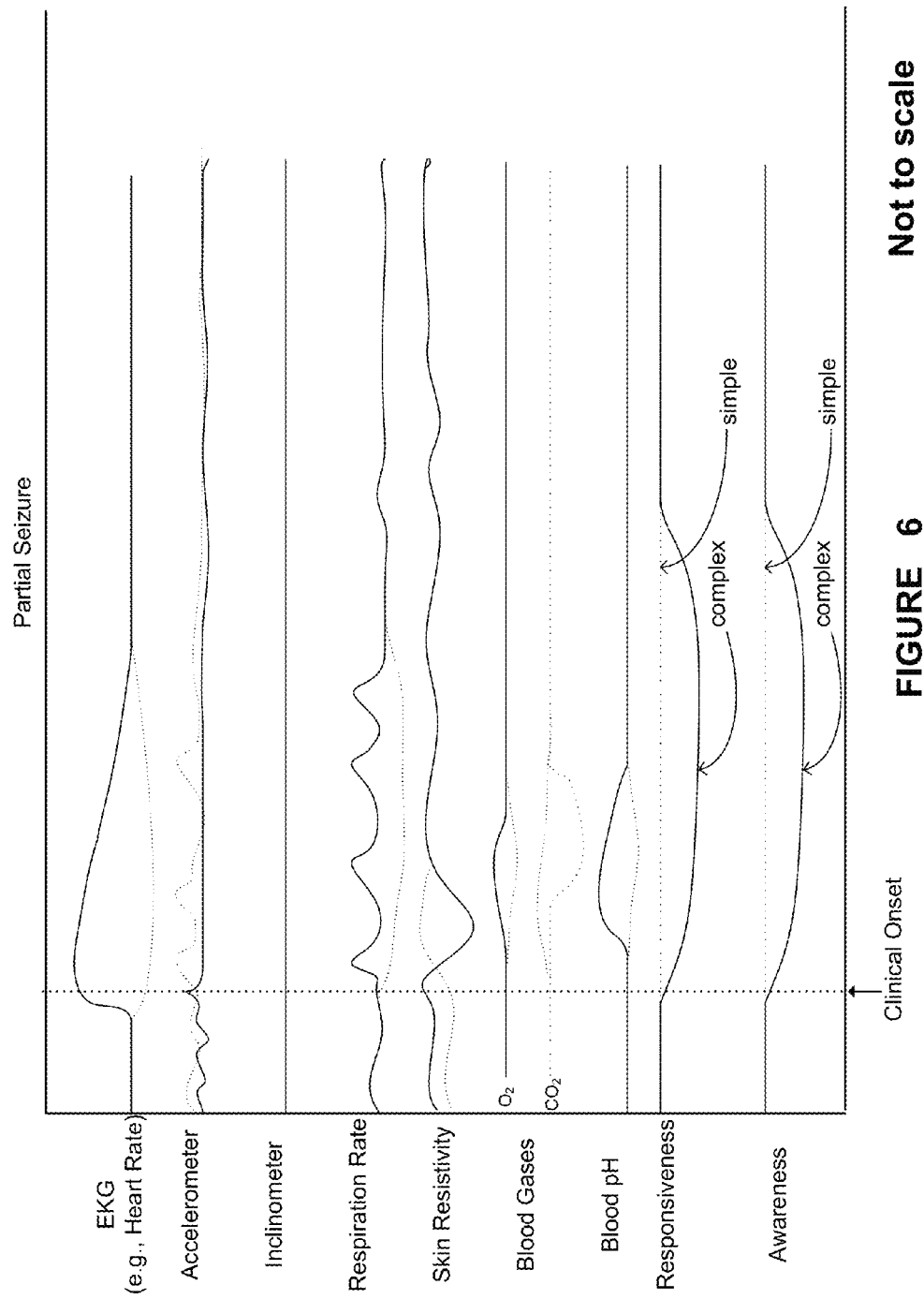
FIG. 6 shows time courses (relative to clinical onset, dashed vertical line) of activity of a plurality of body signals for partial (simple or complex) seizures.

For example, partial seizures are often correlated with increases in respiration rate (see for example, FIG. 6).

In one embodiment, when the autonomic signal is a skin resistivity signal, the detection can be partially based on the observation that some seizure types are associated with a deviation of skin or body temperature from an interictal reference skin or body temperature value range (see for example, FIG. 4).

For example, certain partial seizures are associated with a decrease in skin resistivity (see for example, FIG. 6) and tonic-clonic seizures with an increase in body temperature.

In still another embodiment, when the neurologic signal is an eye signal, the detection can be partially based on the observation that some seizure types are associated with eye position changes (e.g., forced binocular deviation to the right) or the occurrence of abnormal eye movements (e.g., horizontal nystagmus) or both) (see for example, FIG. 4). For example, absence seizures are associated with quasiperiodic blinking (see for example, FIG. 7).

The rate, amplitude and pattern of eyelid blinking may provide information about level of consciousness (e.g., awake vs. asleep or unresponsive) of a patient and during wakefulness. These parameters may allow for differentiation of normal vs. abnormal wakefulness states, e.g., abnormal wakeful state during complex partial and/or absence seizures, the state following termination of complex partial and/or absence seizures, and/or the termination of generalized tonic clonic seizures. Parameters such as blinking rate, amplitude and inter-blinking interval (from which distinctive patterns may be discerned) may be used for detection and quantification of seizures as well as for classification purposes through comparisons with the non-seizure interictal state. Blinking activity, which is a form of kinetic activity, may be recorded using device(s) (e.g., electrodes) placed over or under the skin overlaying the supra- or infraorbital regions or with optical devices.

In one embodiment, when the autonomic signal is a blood signal, the detection can be partially based on the observation that some seizure types are associated with an increase in stress markers (e.g. catecholamines, cortisol, and metabolites thereof) relative to a reference level of the stress marker.

Should stress markers reach a prespecified reference value (which may be different than that used for detection of state change purposes), the patient's total antioxidant capacity and lipid peroxidation intensity may be monitored to institute neuroprotective measures, such as increasing total antioxidant capacity. Neuronal hyper-excitability which occurs in seizures may lead to excessive production of free radicals and eventually to neuronal injury.

Alternatively or in addition, the blood signal can be a blood gas (e.g., O2 or CO2) level or a blood pH level, and the detection can be partially based on the observation that some seizure types are associated with blood gas and/or pH levels outside of an interictal reference value range (see for example, FIG. 4). One or more of the blood signals described above may give information regarding respiratory signals, and vice versa.

For example, tonic-clonic seizures are associated with a drop in arterial O2 concentration, an increase in arterial CO2 concentration, and a decrease in blood pH (see for example, FIG. 5).

For another example, certain partial seizures are associated with a slight increase in arterial O2 concentration, a decrease in arterial CO2 concentration, and a slight increase in arterial pH (see for example, FIG. 6).

In one embodiment, when the neurologic signal is a brain signal, the detection can be partially based on the observation that some seizure types are associated with sudden, transient increases in the amplitude at certain frequencies of cortical waves or with changes in their morphology (e.g., spike-slow wave complexes) (see for example, FIG. 4).

Figure 8:
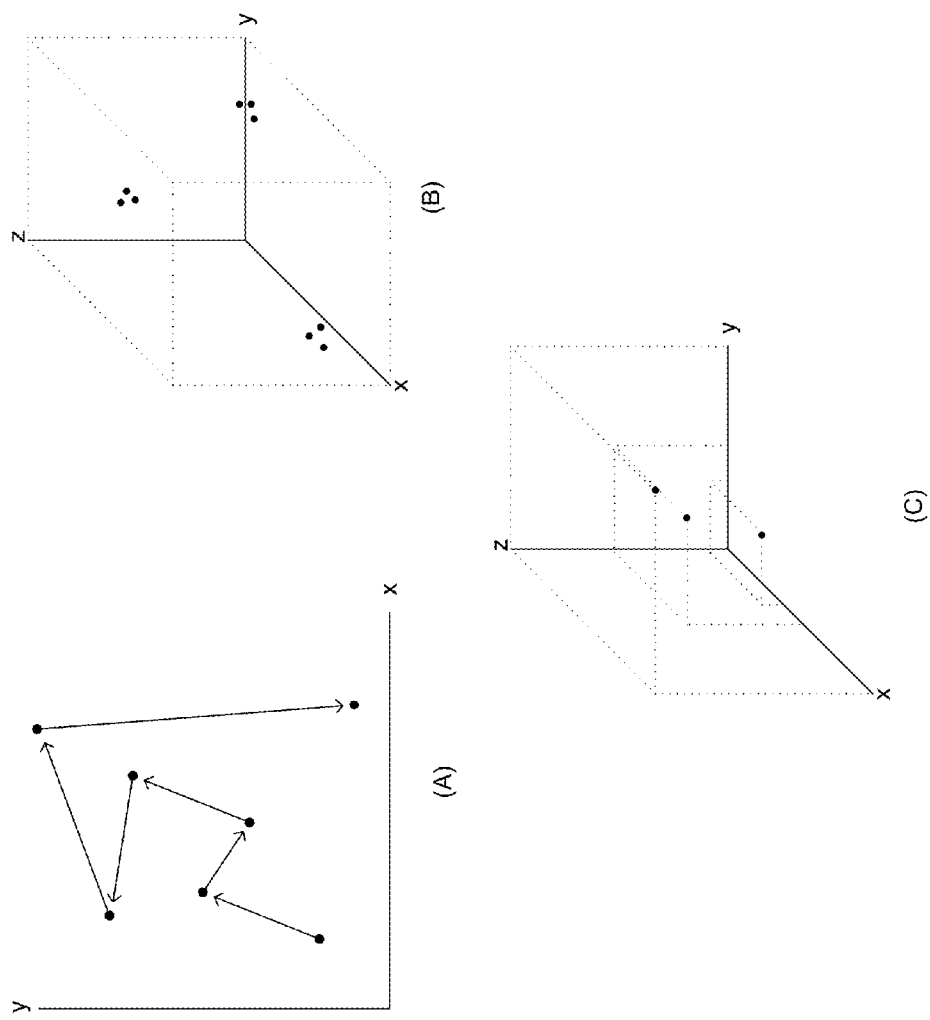
FIG. 8 shows (A) an exemplary two-dimensional plot of a trajectory of epileptic movements, (B) an exemplary three-dimensional plot of epileptic movements, and (C) an additional exemplary three-dimensional plot of epileptic movements.
Figure 9:
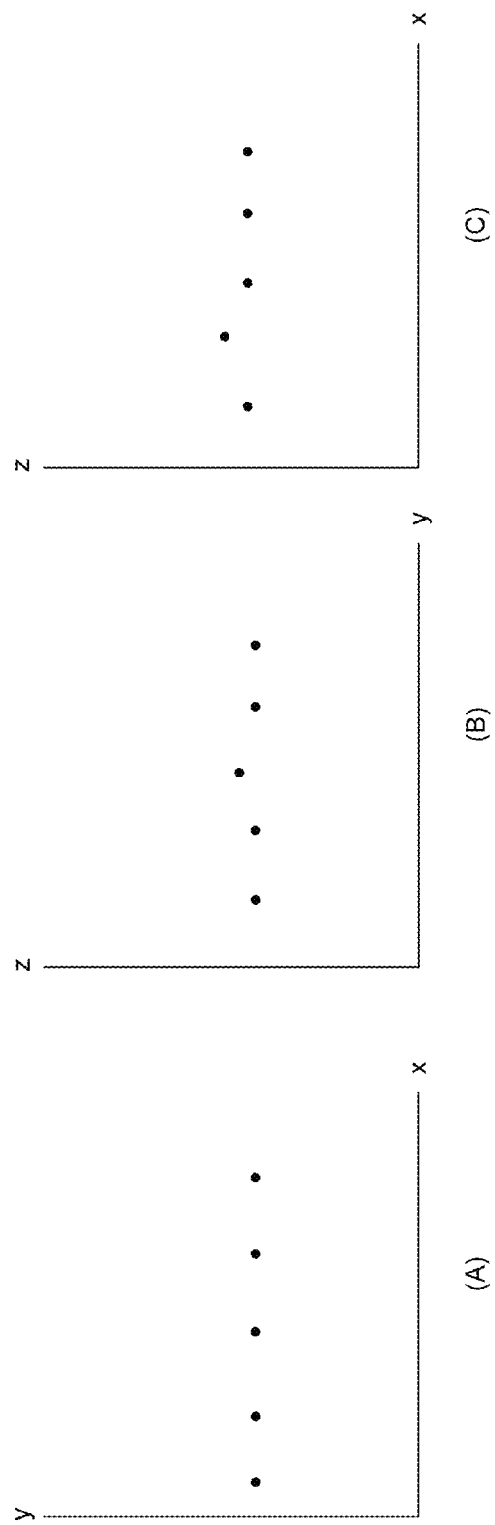
FIG. 9 shows three two-dimensional, temporally cumulative plots of discrete movements during the clonic phase of a primarily or secondarily generalized tonic-clonic seizure.

In one embodiment, when the neurologic signal is a kinetic signal, the detection can be partially based on the observation that some seizure types are associated with increases or decreased in the amplitude and velocity of movements the appearance of particular patterns or sequences of body or appendicular movements, cessation of movements or loss of postural tone or marked increased in body muscle tone as provided by electromyography (EMG), accelerometer, inclinometer, and/or actigraph outputs (see for example, FIG. 4). EMG antigravitatory muscles provides similar information to accelerometers or inclinometers about falls and in certain cases, EMG may replace them. For example, if a patient is in the recumbent position and has a generalized tonic-clonic seizure, the inclinometer and the accelerometer will not detect a fall but the EMG will (indirectly) by showing absence of muscle activity in antigravitatory muscles. This also applies to patients that at the onset of the generalized tonic-clonic seizure are either propped/supported. Falls during certain generalized tonic clonic seizures are caused by increases not decreases in postural muscle tone. Also, while muscle tome may be decreased or increased during partial seizures, the extent (number and type of muscle groups involved compared to generalized tonic-clonic seizures) allows for differentiation. Particular examples of kinetic signals relating to epileptic movements are shown in FIGS. 8-9.

U.S. Patent Application Publication 2009/0124870 to Arends et al. discloses a patient monitoring system using at least one heart rate sensor and a least one muscular tension sensor. The publication does not disclose acquisition or analysis of kinetic activity to monitor a patient. One or more of the embodiments of the present invention provide for detecting seizures through cardiac data (e.g., EKG) used in conjunction with motion data (e.g., accelerometer).

FIG. 8A shows a two-dimensional (x,y) discrete trajectory of epileptic movements (low sampling rate is used to minimize computations but a continuous trajectory may be plotted). This plot contains spatial (in reference to a fiducial marker such as the patient's sternum) and temporal information (when a movement occurs and their order of occurrence) about body movements during an epileptic seizure. The arrows show the sequence of movements. Colors or shapes, instead of arrows may be used to track the temporal evolution of movements. When stereotypical the movement trajectory may be used as a template for detection using for example matched filtering. This plot may be also generated in 3-D.

FIG. 8B shows a three-dimensional (x,y,z) discrete plot of epileptic movements The movements form clusters (3 in this example; the left most and lower most clusters are intended to illustrate interictal movements and the right most cluster, epileptic movements) that may have different shapes or dimensions for each patient. These clusters may be used (e.g., cluster analysis, principal component analysis) for detection, quantification, classification and/or validation of detection of seizures, and optionally as well as for logging, tracking the temporal evolution of seizures, and/or optimization of detection, quantification, classification, and/or of therapy. This plot contains only spatial information; temporal information may be added through the use of arrow or color or shape codes. When stereotypical the movement trajectory may be used as a template for detection using for example matched filtering.

FIG. 8C shows a three-dimensional (x,y,z) discrete plot of epileptic movements; notice that one movement occurs only in 2-D (low sampling rate is used to minimize computations but a continuous trajectory may be recorded. This plot contains only spatial information (in reference to a fiducial marker such as the patient's sternum); temporal information may be added through the use of arrow or color or shape codes. When stereotypical the movement trajectory may be used as a template for detection using for example matched filtering.

FIG. 9 shows three two-dimensional, temporally cumulative plots of discrete movements during the clonic phase of a generalized (primarily or secondarily) tonic-clonic seizure. The first movement in the sequence is located closest to the x,y axes intersection and subsequent ones are plotted to the right of the preceding movement and in the order in which they occur. For ease of visualization there are 3 plots ((A) x,y; (B) y,z; (C) x,z). The vertical and horizontal axes provide information about amplitude and the horizontal axis also provides temporal information (e.g. inter-movement interval). In this illustration, the movements occur at equal time intervals and are periodic as is common in the clonic phase of a generalized seizure. When stereotypical the movement trajectory may be used as a template for detection using for example matched filtering.

U.S. Patent Application Publication 2009/0137921 to Kramer et al (Kramer) describes using accelerometer data to compare against previously stored motion data that are not confined to epileptic events. One or more of the embodiments of the present invention provide for detecting seizures through cardiac data (e.g., EKG) used in conjunction with motion data (e.g., accelerometer). Embodiments of the present invention may provide for detecting seizures using less specific motion data since the cardiac and motion data may be used to confirm each other.

Herein, one or more of the direction, speed/acceleration, trajectory (1D to 3D), pattern, and quality of movement may be termed a characteristic of movement. Such characteristics of movement may be determined for particular movements and used to distinguish among ictal, post-ictal, and interictal motor activity.

Figure 7:
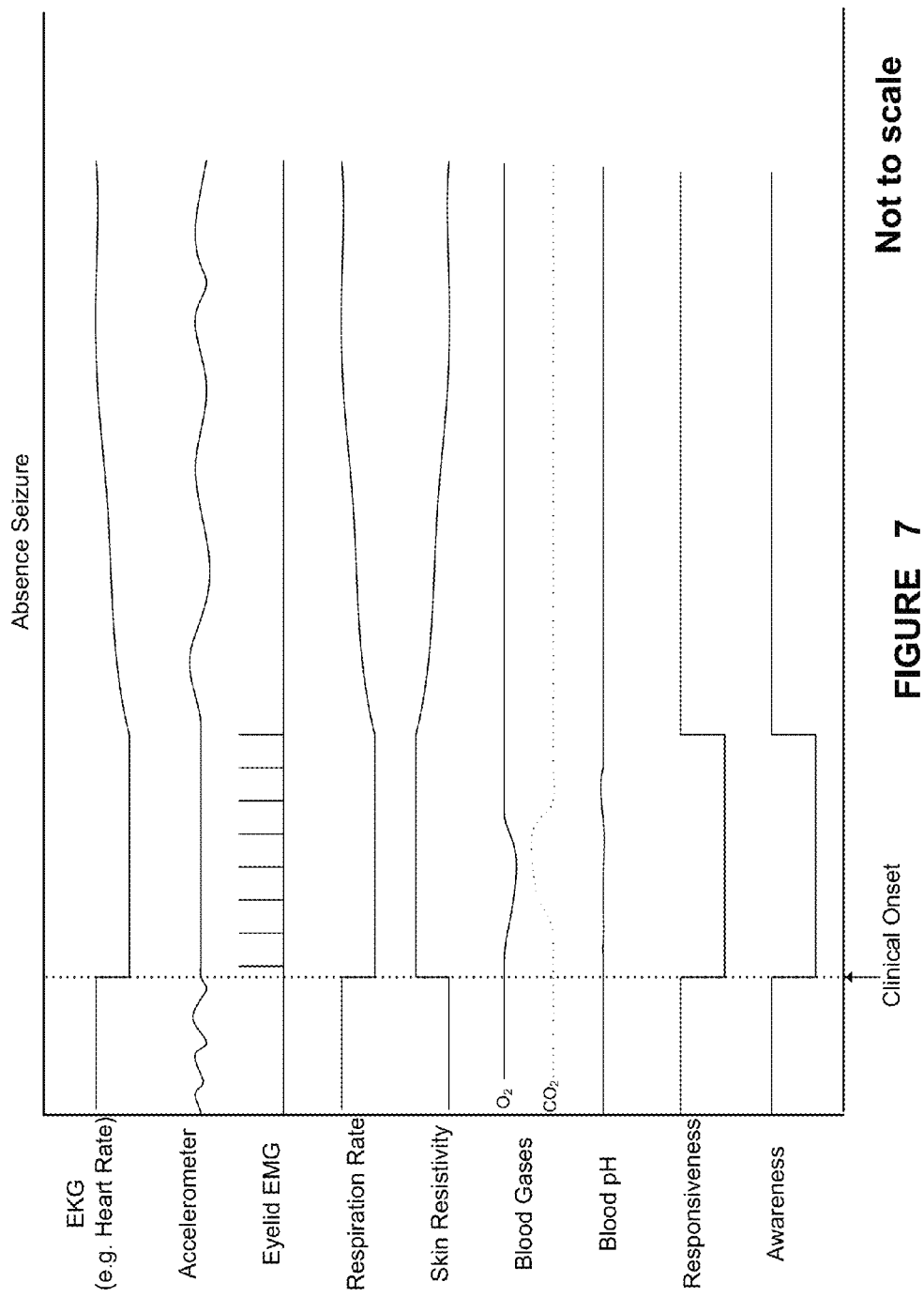
FIG. 7 shows time courses (relative to clinical onset, dashed vertical line) of activity of a plurality of body signals for idiopathic absence seizures.

For example, absence seizures are typically correlated with a cessation of body movements and temporary but complete loss of responsiveness and awareness (see for example, FIG. 7).

For another example, tonic-clonic seizures are associated with losses of responsiveness and awareness, and falls to the ground if the patient is standing at onset. Common characteristics of movement include a "spike" in the inclinometer's output at seizure onset (e.g., if the patient was standing, the seizure will cause him to fall), a quiet period of accelerometer output after seizure onset (e.g., the tonic phase), and a series of quasiperiodic "spikes" (e.g., at around 3 Hz) in accelerometer output after the tonic phase (e.g., the clonic phase), followed by cessation of body movements. The tonic phase presents with a marked increase in EMG activity in axial and appendicular muscles. Also, a "spike" in inclinometer output during or after the post-ictal phase may be seen (e.g., the patient rises after a fall at seizure onset) (see for example, FIG. 5).

For yet another example, certain partial seizures are often correlated with a quiet period of accelerometer output after seizure onset (see for example, FIG. 6), while others characterized by an increase in involuntary movements and vocalizations (e.g., so called "hypermotoric" seizures).

Generally, movement characteristics, qualities, and loci are similar, if not stereotypical, among tonic-clonic seizures and certain partial seizures for a particular patient, and are also similar among patients with these seizure types. Thus, patterns can often be obtained and used for detection, quantification, and classification. However, in certain partial seizures, movements may differ not only between patients but also between seizures of the same patient.

In some embodiments of this invention, the number, type, and placement of motion sensors to be used in detecting, quantifying, and/or classifying movement can be based on (a) degree of movement similarity between seizures, (b) the signal-to-noise ratio of data from the locus or loci (e.g., body parts such as eyes, head, limbs, trunk, etc.), and/or (c) patient safety and device longevity considerations, among others. These considerations can be taken into account to maximize speed and/or accuracy of detection, quantification, and/or classifying, and/or performing this task or tasks in a monetary and/or computationally cost-effective manner.

For example, if a patient's tonic-clonic seizures are consistently preceded by a deviation of the head to the right, a single motion sensor (e.g., placed in this case on the head or over/in a neck muscle involved in the movement) may be sufficient to detect the motion and characterize the seizure. If the patient's seizures are characterized by sudden falls, again, a single device, placed in a body part that will have most acceleration or range of displacement, may be sufficient for seizure detection, quantification and classification purposes. If the patient's seizures are frequently secondarily generalized seizures, a plurality of devices, with at least one situated on each of the left and right sides of the body and/or with at least one situated on the upper and lower portions of the body may be desirable to provide sufficient sensitivity and specificity for seizure detection and characterization.

The choice of number of sensors, their type (e.g., whether they are sensitive to mechanical or electrical signal changes), and their placement can be optimized for each seizure type and patient.

In one embodiment, when the neurologic signal is a brain signal, the detection can be partially based on the observation that some seizure types are typically correlated with a decrease in responsiveness (see for example, FIG. 4).

For yet another example, partial seizures can often be distinguished between simple and complex based on changes in the patient's responsiveness. Simple partial seizures are associated with preservation of awareness and memory for the events that occurred during the seizure and responsiveness may or may not be preserved, whereas complex partial seizures are invariably characterized by impairment in the patient's unawareness of their surroundings and anterograde amnesia spanning a certain time period (see for example, FIG. 6). Responsiveness is tested by having the patient perform certain motor actions (e.g., press a button; raise an arm) and/or cognitive tasks (e.g., answer questions). Awareness may be tested by measuring a patients ability to recollect events that occurred during a certain period of time or by administering memory tests. The number of words, images or events correctly recalled allow quantification of the degree of awareness (compared to an inter-ictal reference value). In one embodiment, the method further comprises providing a responsiveness test and awareness tests to assess patient's responsiveness and awareness, and characterizing the epileptic event based upon the speed and appropriateness or correctness of the responses to neuropsychologic tests.

For example, the following table shows conclusions that can generally be drawn from determinations of whether a patient remains responsive ("Responsive?") and/or remains aware ("Aware?") during a seizure.

| Responsive? | Aware? | Reasonable conclusion |
|---|---|---|
| Yes | Yes | Not a complex partial or secondarily generalized seizure |
| Yes or No | No | Complex partial seizure |
| No | Yes | Simple partial seizure interfering with ability to respond |
| No | No | Complex partial or primarily or secondarily generalized seizure |

The autonomic signal and the neurologic signal can be used to detect a seizure; to quantify its severity; to classify a seizure as to its type (e.g., absence, tonic-clonic, simple partial, complex partial); and/or to validate an identification or detection of a change of state as corresponding to a seizure.

The features of the two or more signals on which a detection or other action of the present invention is based may occur simultaneously or in any temporal relationship. In one embodiment, the temporal relationship between two signals is as set forth in FIGS. 4-7 and as described above. Relative temporal relationships between the body signals may be used indentify, validate, classify, and/or quantify an epileptic event. Information relating to the timing of any two body signals, e.g., an increase in heart rate before, after, or substantially simultaneously with accelerometer data suggestive of a seizure, may be used to identify an epileptic event, validate an identification of an epileptic event, quantify an epileptic event's severity, intensity, or duration, and/or classify a seizure.

The various embodiments recited above may be also used to distinguish epileptic generalized from non-epileptic generalized seizures whose kinetic activity, but not patho-physiology, resembles that of epileptic seizures. Non-epileptic generalized seizures, also known as pseudo-seizures, psychogenic seizures, or hysterical seizures, are often misdiagnosed as epileptic at large cost to the patient, caregivers, and the health care system. A multimodal signal approach relying heavily on kinetic, autonomic and metabolic signals is ideally suited for diagnosing identifying and classifying seizures as non-epileptic given its high sensitivity and specificity and cost-effective (no hospital admission would be required as this invention's methods are implementable in small portable devices).

The following are a few examples of differences with high discriminatory values, one or more of which can be used to distinguish between epileptic generalized seizures and non-epileptic generalized seizures: a) The intensity of non-epileptic movements, unlike that of epileptic movements, waxes and wanes (crescendo-decrescendo pattern) throughout the event; b) Non-epileptic movements, unlike epileptic movements, are multi-directional or multi-planar, said changes in direction occurring very rapidly and in a random sequence. For example, vertical movements may give way to horizontal ones and these in turn to oblique or rotary or flapping movements; c) Joint movements in non-epileptic seizures, unlike in epileptic seizures, are incoherent or disorganized: while the right upper extremity is moving in the vertical plane at a certain speed and with certain amplitude and phase, the direction, speed, phase and amplitude of movement of the left upper extremity may be different at the same time; d) in non-epileptic seizures, unlike in epileptic seizures, co-activation of agonists and antagonists muscle groups is rarely seen:

Co-activation of the abdominal and paraspinal muscles during an epileptic generalized tonic-clonic seizure keeps the torso straight while the sole activation of paraspinal muscles, a common observable in non-epileptic generalized seizures, manifests as an arched back; e) Involvement (in the form of movements) of certain body parts is commonly found in non-epileptic seizures while they are rarely if ever seen in epileptic generalized seizures; pelvic thrust, pelvic gyrations, and other pelvic movements are nearly pathognomic of non-epileptic seizures; f) Metabolic (lactic) acidosis occurs with epileptic generalized tonic-clonic seizures and not with non-epileptic generalized seizures.

Detection can be conducted by any appropriate technique. For example, each signal may be recorded, conditioned, and processed using hardware (e.g., DC or AC amplifiers), gains or amplification, filters and sampling rates appropriate for the spectral properties, and/or time-scale and characteristics of each signal. Each signal may be analyzed whole or after decomposition using suitable digital or analog signal processing techniques. The decomposition may be performed using any of the following techniques: Fourier transform based methods, wavelets, customized FIR or IIR filters, intrinsic time scale decomposition, wavelet transform maximum modulus, or any other technique which may decompose the signal based on its spectral properties, morphology or waveform, site of origin or generation, its position regarding a baseline, zero-crossings and circadian or ultradian rhythms. In the case of a decomposed signal none, one, or more of the components may be discarded if it is deemed of little value for detection of change of brain/body state. These data, as they stream through the system, may be analyzed in windows of appropriate length for each signal (e.g., signal-based customized window approach). This window corresponds to a foreground which may be referenced for quantitative purposes to a background, consisting of past data. The length of the background window may be determined by the properties of the signal under study and the time scale of the patterns or events which are the subject of detection. Any of these features or parameters may be adapted as needed to account for circadian or other influences to the signals Although the above paragraph emphasizes hardware for signal conditioning and other tasks, the person of ordinary skill in the art is aware that software, firmware, or other implementations of one or more of the techniques discussed above may be used.

Change in a given signal feature may be associated with one, more than one or none of the brain/body state changes of interest. Reciprocally, changes in brain state may be associated with only one signal feature change, two or more, or none. Each signal feature may be tracked individually and its changes may be subjected to statistical, cluster, Poincaré plot, and/or other forms of analyses to identify changes which are significantly correlated with pathological brain/body state changes such as seizures, movement disorders or with physiological ones such as sleep, attention or cognitive processes. These analyses may yield selectivity (Sl), sensitivity (Se) and specificity (Sp) for each signal feature and may be used to assign values to each of them. The type/number of signal feature used for on-line, real-time detection of changes in brain/body state may be chosen using a value system based on the degree of selectivity (Sl), sensitivity (Se) and specificity (Sp) of each signal feature.

Selectivity is given by the fraction or proportion of type of state changes with which a signal feature is associated. For example, if a state change is associated with only one signal feature change the selectivity would be 1 (1/1) or if it is associated with 2, selectivity would be 0.5 (1/2).

Sensitivity is given by the fraction of detected changes in signal feature over all detectable changes in signal features; for example, if there are 20 state changes/day and 10 of these are detected using a certain signal feature, sensitivity for this signal feature in this case would be 0.5 (10/20).

Specificity is given by the fraction of detected true changes over all detections; for example, if there were 20 detections using a certain signal feature but only 10 corresponded to true brain/body state changes, the signal feature's specificity would be 0.5 (10/20).

The value (for detection purposes) of each signal feature for a particular brain or body state (e.g., ictal, pre-ictal, post-ictal, or interictal, among others) (f) is the product of selectivity (Sl), sensitivity (Se) and specificity (Sp); [f=Sl×Se×Sp]. The closer the value to 1 (which is the maximum possible), the more powerful the signal feature may be considered to be. This value, f, may determine the number of signal features necessary to maximize the probability of accurate and reliable detection of brain/body change of state: Any signal feature with a value of 1 may be used as the only detection signal feature. Signal features with value f<1 may be sorted out, ranked, and added to obtain a summed weighted index F, (F=fEKG+fEOG+ . . . +fTT). F may be calculated in real-time, if the computations required can be performed at an acceptable power expense, or off-line if this is not the case. For example, if data analysis in a certain subject reveals that seizures are accompanied by acceleration in heart rate and this change has selectivity, sensitivity and specificity of 1 so that fEKG=1, this signal feature may be chosen as the only one for automated detection purposes. However, if fEKG<1, other f values, as many as needed or desired, may be added, to reach or approach a desirable high value, such as 1, if the computations can be performed in real-time at an acceptable power cost.

For a particular example, consider a situation where the signal feature values are [fEOG=0.40; fEKG=0.45; fPKG=0.10; fSkT=0.15; fEMG=0.12; fAt=0.14; fTT=0.09]; these values are sorted out and ranked from highest to lowest [fEKG=0.45; fEOG=0.40; fSkT=0.15; fAt=0.14; fEMG=0.12; fPKG=0.10; fTT=0.09] and as many values as needed are added to obtain F=~1 (e.g., in this case, F=0.45+0.40+0.15=1; in this case 3 values sufficed to reach 1. It should be noted that in certain cases, addition of all indices may not equal 1, in which case detection of state changes may be issued if and when F is greater than a lower number, such as 0.5. Threshold (T), duration (t) other constraints (such as time of day or patient's state (awake vs. asleep; resting wakefulness vs. exercise) may be introduced to improve accuracy of detection, if desired.

Another metric of interest is the property defined herein as degree of signal ubiquitousness (U) denoting the number of different states during which the same signal feature changes. For example, cardiac activity is highly ubiquitous since increase in heart rare occur during different normal (exercise, emotion) and abnormal states (seizures, cardiac arrythmias), while metabolic (lactic) acidosis would be absent from all, save only generalized tonic-clinic seizures and in extreme/endurance exercise, a rare practice. Ubiquitousness (U) is the fraction of a signal feature present in various states over the total number of states. The ubiquitousness (U) of heart rate in the example above, is 1 since it occurs in 4/4 states while that of lactic acidosis is 0/4 or at most 1/4 if extreme exercise is included. U may replace Sl in the calculation of F to optimize performance of state detection changes. While in certain cases U is the reciprocal of Sl. There may be certain cases in this relation does not apply and U maybe more useful. As stated, in one embodiment, detecting the epileptic event is based on an autonomic signal and a neurologic signal. In one embodiment, an algorithm can receive as inputs both the autonomic signal and the neurologic signal and process them together to yield an output indicative of a detection or a non-detection. In another embodiment, detecting the epileptic event comprises identifying a putative epileptic event based on one of the autonomic signals (e.g., cardiac signals as measured by EKG) and one of the neurologic signals (e.g., kinetic signals as measured with an accelerometer, an inclinometer, or an actigraph), and validating the identifying based on one of the other of the autonomic signals (e.g., respiration) and one of the other neurologic signal (e.g., responsiveness test, memory test, comprehension tests, etc.).

Another metric of interest is Positive Predictive Value (PPV), defined as:

(number of True Positives)/(number of True Positives+number of False Positives)

Regardless how the detection is made, in one particular embodiment, the present invention relates to a method for detecting an epileptic event based upon a patient's cardiac signal and kinetic activity, comprising providing a cardiac signal indicative of the patient's heart beats; providing a kinetic signal indicative of a body movement of the patient; and detecting an epileptic event based upon the cardiac signal and the kinetic signal.

The cardiac signal may be electrical, acoustic, thermal, or any other cardiac signal detectable using certain equipment or tools. In one embodiment, the cardiac signal is provided by an electrocardiogram (EKG).

The kinetic signal can be provided by a device capable of recording any of the attributes inherent to movement such as amplitude, velocity, direction, trajectory and quality. In one embodiment, the kinetic signal is provided by an accelerometer, an inclinometer, or an actigraphic device. An actigraphic device or actigraph can be considered as being both an accelerometer and an inclinometer. An exemplary plot of trajectories is shown in FIG. 8A. An exemplary plot of clusters of positions is shown in FIG. 8B.

In one embodiment, the present invention relates to a method for detecting an epileptic event based upon a patient's cardiac signal and kinetic activity, comprising providing a kinetic signal indicative of a body movement of the patient; calculating based on the kinetic signal a kinetic score indicative of a correlation of said kinetic signal with an epileptic event; detecting an epileptic event based upon the patient's heart beat sequence; and providing an output indicative of an epileptic event based on the kinetic score.

In another embodiment, the method comprises providing a cardiac signal indicative of a cardiac activity of the patient; calculating based on the cardiac signal a cardiac score indicative of a correlation of said cardiac signal with an epileptic event; detecting an epileptic event based upon the patient's kinetic activity; and providing an output indicative of an epileptic event based on the cardiac score.

These are both examples of detecting an epileptic event based upon multimodal data, using a plurality of modes of data (e.g., a cardiac mode signal and a kinetic mode signal).

The kinetic signal indicative of a body movement of the patient can be as described above. A kinetic score can be calculated and/or the kinetic signal can be classified as either an epileptic event kinetic signal or a non-epileptic event kinetic signal based on the practitioner's knowledge (e.g., the practitioner is aware certain kinetic signals, e.g., inclinometer spikes, periods of increased accelerometer activity, periods of decreased accelerometer activity, periods of actigraph activity outside of normal ranges, timewise correlations of such signals, etc.), by prior correlation of a patient's kinetic signals with his or her seizures identified by autonomic (e.g., EKG), neurologic (e.g., EEG or direct or indirect clinical observation) endocrine, metabolic (e.g., pH), stress marker (e.g., cortisol) etc., or a combination thereof.

Imaging (e.g., video, thermography, etc.) and/or audio recordings of the patient may be used qualitatively or quantitatively to detect and/or validate the detection of seizures. Detection or validation may be made on- or off-line via human visual analysis or using algorithms that compare one or more of position, velocity, direction, or trajectory of movement of any body part during seizures to non-seizure movements. The time between consecutive movements, the total duration of epileptic movements, and/or their quality (e.g., jerky or smooth) may be also used for detection and/or validation of seizures.

Detecting a possibility of an epileptic event based upon the patient's heart beat sequence can make use of the cardiac-based seizure detection approaches discussed above. For example, noting an increase in the patient's heart rate relative to an interictal reference value is one embodiment of "detecting an epileptic event," e.g., a period of increased likelihood of a seizure.

Upon classifying the kinetic signal and detecting the possibility of the epileptic event based upon the patient's heart beat sequence, an output indicative of an epileptic event can be provided if the kinetic signal is classified as an epileptic event kinetic signal; and an output indicative of the non-occurrence of an epileptic event can be provided if the kinetic signal is classified as a nonepileptic event kinetic signal. This method can validate a cardiac-based seizure detection by use of kinetic signals.

In another embodiment, the present invention relates to a method for detecting an epileptic event based upon a patient's cardiac signal and kinetic activity, comprising providing a kinetic signal indicative of a body movement of the patient; classifying the kinetic signal as either an epileptic event kinetic signal or a nonepileptic event kinetic signal; detecting an epileptic event based upon changes in the patient's heart beat sequence; confirming the detecting if said kinetic signal is classified as an epileptic event kinetic signal; overriding the detecting if said kinetic signal is classified as a nonepileptic event kinetic signal; and providing an output indicative of an epileptic event only if the detecting is confirmed.

In yet another embodiment, the present invention relates to a method for detecting a tonic-clonic epileptic seizure whether primarily or secondarily generalized (i.e., whether the seizure emerges in both hemispheres of the brain at substantially the same time (primary) or whether it emerges at a particular focus and then spreads (secondary) based upon two or more of a patient's body signals, comprising: providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; an isometric force signal indicative of the patient's muscle activity; a sound signal indicative of the patient's oral utterances or vocalizations; an ocular signal indicative of the patient's eye position and movements; a responsiveness signal indicative of the patient's responsiveness; and a stress marker signal indicative of at least one stress marker of the patient; and detecting the generalized tonic-clonic epileptic seizure based upon the timewise correlation of two features, one feature being of each of the at least two body signals, wherein:

the feature of the cardiac signal is an increase in the patient's heart rate above a reference value;

the feature of the accelerometer signal is an increase in the velocity, amplitude or number of movements per unit time of said patient above a reference value followed by a decrease in the patient's movement below a reference value;

the feature of the inclinometer signal is a rapid change of the patient's body position indicative of a fall;

the feature of the respiratory signal is a brief apnea followed by hypopnea and after the end of the seizure by a transient increase in respiratory rate, tidal volume, and minute volume;

the feature of the skin resistivity signal is a skin resistivity outside an interictal reference value range;

the feature of the blood gas signal is a decrease in the patient's arterial blood oxygen content below an interictal reference value and an increase in arterial carbon dioxide content above an interictal reference value, or both;

the feature of the blood pH signal is a decrease in the patient's blood pH below an interictal reference value;

the feature of the isometric force signal or EMG activity is a transient increase in the patient's muscle contractions above an interictal reference value that may be preceded or followed depending on the seizure type (e.g., primarily vs. secondarily generalized) and patient by a loss of muscle tone or of EMG in anti-gravitatory muscles the feature of the sound signal is a distinctive sound referred to as a patient's an "epileptic cry";

the feature of the ocular signal is a deviation of the patient's eye's often upwardly;

the feature of the responsiveness signal is a decrease in the patient's responsiveness below an interictal reference value;

and the feature of the stress marker signal is an increase in at least one stress marker of the patient above an interictal reference value.

In one embodiment, this method further comprises indicating the end of the generalized tonic-clonic epileptic seizure when the value of one or more of the features listed above falls outside the range of values for both the ictal and inter-ictal states for that patient.

Alternatively or in addition, in one embodiment, this method further comprises indicating the beginning of a post-ictal period based upon the appearance of at least one post-ictal feature of at least one said body signal, wherein:

the post-ictal feature of the cardiac signal (e.g. heart rate) is outside the range of values for the ictal and interictal periods for that patient and within the range of postictal values;

the post-ictal feature of the accelerometer signal is a cessation of the patient's seizure movements; the post-ictal feature of the respiratory signal is a transient increase in the patient's respiratory frequency, tidal volume, and/or minute volume, such as may follow periods of apnea and hypopnea and the patient's seizure movements; and the post-ictal feature of the responsiveness and of the awareness signal is the persistence in the patient's unresponsiveness and unawareness. As should be apparent, "unresponsiveness" and "unawareness" are distinct phenomena; a person may be aware of stimuli (and able to form memories of said stimuli and the context in which they occurred) but unable to respond thereto, and vice versa. Responsiveness as used herein refers to the ability to respond reflexively or adaptive/purposefully; this distinction may be used for seizure classification purposes.

The term "post-ictal," is not necessarily limited to the period of time immediately after the end of the primarily or secondarily generalized tonic-clonic epileptic seizure and is not limited to this type of seizure but also encompasses partial seizures (e.g., all complex and certain simple partial and absence seizures). Rather, it refers to the period of time during which at least one signal has one or more features associated with the period following the cessation of a seizures that indicates one or more of the patient's body systems are not functioning normally (e.g., as a result of the seizure or of an injury suffered during the seizure) but are not exhibiting features indicative of a seizure.

In a further embodiment, this method further comprises indicating the end of the post-ictal period and the beginning of the inter-ictal period when the values of at least one of the post-ictal features changes to being within the range of reference body signal values or behavior associated only with the inter-ictal period wherein:

the cardiac signal returns to a heart rate within a range indicative of an interictal state for said patient the accelerometer signal of the patient's movement velocity, amplitude or number of movements per unit time returns to values indicative of an inter-ictal state for said patient;

the accelerometer signal is a movement pattern including inter-movement intervals or trajectory indicative of that patient's inter-ictal period the respiratory signal (e.g., rate, tidal volume, minute volume, and pattern) returns to a range indicative of the inter-ictal state for that patient; the responsiveness signal returns to its range of inter-ictal values for that patient; and the patient's awareness returns to inter-ictal ranges for the patient.

The changes in signal features (e.g., responsiveness, awareness, heart activity, respiratory activity, etc.) during the transitions (e.g., inter-ictal to ictal, ictal to post-ictal and post-ictal to interictal) that make up the epileptic cycle, may or may not occur simultaneously or synchronously; certain signal feature values change ahead or behind others. Thus, using these signal features, the transitions may be qualitatively classified into (a) partial or complete; (b) quantitatively as the fraction of signal features (numerator) that transitioned into or out of the state over the total number of signal features that have been observed (denominator).

For example, if only 2/4 signal feature values indicative of the transition from ictal to postictal or from post-ictal to inter-ictal have reached values within the range of the new state, the is classified as partial assigned an score of 0.5 and declared complete only when all (e.g., 4/4 in this example) signal features values are within the range of indicative of the new state at which time the transition is deemed completed.

The transitions may be also quantified using the: a) magnitude of the change in feature signal values measured for example as the increase in seizure energy (see Osorio et al, Epilepsia 1998, 2001) as compared to its inter-ictal value, or the percent of incorrect responses to a complex reaction time test compared to the responses in the inter-ictal state, or the lengthening in response time regardless of correctness of responses (see, e.g., U.S. Ser. No. 12/756,065, filed Apr. 7, 2010, which is hereby incorporated herein by reference) compared to that recorded in the inter-ictal state for that patient; b) rate of change in the signal features measured for example as the time to peak value change measured from the onset time of the transition or the time to first error in a complex reaction time compared to those obtained in the inter-ictal period; c) duration (e.g., in seconds) of the state change from the onset of the inter-state transition to the beginning of the transition from the present state (e.g., ictal) to another state (e.g. postictal). These metrics may be used to e.g., assess the disease state (e.g., the duration and magnitude of the ictal state are increasing over time) and also the efficacy of therapeutic interventions. Shortening the magnitude of the changes (e.g., degree of unresponsiveness) in signal feature values from the inter-ictal range to the ictal value or the transition time between the post-ictal and interictal periods provide evidence that the therapy is beneficial while increases in the magnitude or duration of the changes in feature signals from the interictal range to ictal value or a lengthening of the transition from the post-ictal to the interictal state are evidence of an adverse therapeutic effect. The qualitative and quantitative categorization of the various states and of their transitions is applicable to all seizures and epilepsy types and also to other states and inter-state transitions.

Analogously to detecting tonic-clonic seizures, in one embodiment, the present invention relates to a method for detecting a partial epileptic seizure based upon two or more of a patient's body signals, comprising providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an arterial blood gas signal indicative of the patient's blood oxygen content, carbon dioxide content, or both; an arterial blood pH signal indicative of the patient's blood pH; a sound signal indicative of the patient's oral utterances or vocalizations or breathing; a responsiveness signal indicative of the patient's responsiveness; an endocrine signal indicative of seizures and a stress marker signal indicative of the occurrence of tissue stress; and detecting the partial epileptic seizure based upon the timewise correlation of two features, one feature being of each of the at least two body signals, wherein:

the feature of the cardiac signal is a patient's heart rate outside an interictal reference value range;

the feature of the accelerometer signal is a movement outside an interictal reference value range;

the feature of the respiratory signal is a respiration rate, tidal volume, and/or minute volume outside an interictal reference value range;

the feature of the skin resistivity signal is a skin resistivity outside an interictal reference value range;

the feature of the arterial blood gas signal is an arterial blood oxygen content outside an interictal reference value range, an arterial carbon dioxide content outside an interictal reference value range, or both;

the feature of the blood pH signal is a blood pH outside an interictal reference value range;

the feature of the sound signal is a change in the patient's oral utterances or vocalizations outside an interictal reference value range;

and the feature of the stress marker signal is an increase in the patient's endocrine or stress markers above an interictal reference value.

Partial seizures can be distinguished from generalized seizures. Partial seizures that evolve into secondarily generalized seizures can also be distinguished from primarily generalized seizures. Also, within the class of partial seizures, simple partial seizures can be distinguished from complex partial seizures.

In a further embodiment, this method further comprises classifying the partial epileptic seizure as a complex partial seizure if a feature of the awareness signal timewise correlated with the at least one body signals is a decrease in the patient's awareness or other cognitive functions below an interictal reference value, and as a simple partial seizure if the patient's awareness or other cognitive function remain at or above an inter-ictal reference a feature of the awareness s signal timewise correlated with the at least two body signals.

Alternatively or in addition, in one embodiment, the method further comprises indicating the end of the partial epileptic seizure when at least one of the signal features the respective body signal is outside the range of values for the ictal and interictal periods for that patient and within the range of postictal values;

Alternatively or in addition, in one embodiment, the method further comprises indicating the beginning of a post-ictal period based upon the appearance of at least one post-ictal feature of at least one said body signal, wherein:

the cardiac signal is a heart rate outside an ictal reference value range and within a range indicative of a post-ictal state for said patient;

the accelerometer signal is a movement velocity, amplitude, or number of movements per unit time outside an ictal reference range of values and within a range indicative of a post-ictal state for said patient;

the accelerometer signal is a movement pattern, trajectory, or inter-movement intervals outside an ictal reference value range and within a range indicative of a post-ictal state for said patient;

the respiratory signal is a respiration rate outside the ictal range of values for that patient and within a post-ictal range for said patient;

the responsiveness signal is a change in the patient's unawareness or cognitive dysfunction to a value outside both of an ictal range and an interictal range; and the awareness signal is a change in the patient's awareness to a value outside both an ictal range and an interictal range.

In a further embodiment, the method further comprises indicating the end of the post-ictal period when each of the features from the respective body signal returns to the range of values associated with the interictal period.

Alternatively or in addition, in one embodiment, the method further comprises indicating the beginning of the inter-ictal period based upon the appearance of at least one inter-ictal feature of at least two said body signal, wherein:

the inter-ictal feature of the cardiac signal is a return of the patient's heart rate values to inter-ictal reference values and outside a range indicative of a post-ictal and ictal state for said patient;

the inter-ictal feature of the accelerometer signal is a return of the patient's movement velocities, amplitudes, or number of movements per unit time to the inter-ictal value range for that patient and outside the values or patterns indicative of a post-ictal and ictal states;

the inter-ictal feature of the accelerometer signal is a return of the movement patterns or trajectories to those present in the inter-ictal period for that patient and different from those present during the post-ictal and ictal states;

the inter-ictal feature of the respiratory signal is return of the respiratory frequency to inter-ictal values for that patient and outside those indicative of post-ictal and ictal states;

the inter-ictal feature of the responsiveness signal is a return of the patient's responsiveness to a range of values seen in the inter-ictal state for that patient and outside a range of values indicative of post-ictal and/or ictal states the inter-ictal feature of the awareness signal is a return of the patient's awareness to a range of values seen in the inter-ictal state for the patient and outside a range of values indicative of post-ictal and/or ictal states.

Regardless of how an epileptic event is detected, in some embodiments, a responsive action may be taken selected from warning, logging the time of an epileptic event, computing and storing one or more seizure severity indices, or delivering a therapy to prevent, abate or lessen the severity of the ictal or postictal states. Further responsive actions such as warning, logging and treatment may be taken if the ictal or postictal states severity exceeds for example the 90th percentile values for a patient.

A warning may be given as, for example, a warning tone or light implemented by a medical device or a device adapted to receive indications of the seizure; as an automated email, text message, telephone call, or video message sent from a medical device or a unit in communication with a medical device to the patient's cellular telephone, PDA, computer, television, 911 or another emergency contact number for paramedic/EMT services, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

The time may be logged by receiving an indication of the current time and associating the indication of the current time with an indication of the epileptic event.

Seizure severity indices may be calculated and stored by appropriate techniques and apparatus.

A seizure may be treated by appropriate techniques, such as those discussed below. The treatment may be one or more treatments known in the art. In one embodiment, the treatment comprises at least one of applying an electrical signal to a neural structure of a patient; delivering a drug to a patient; or cooling a neural structure of a patient. When the treatment comprises applying an electrical signal to a portion of a neural structure of a patient, the neural structure may be at least one of a portion of a brain structure of the patient, a portion of a cranial nerve of a patient, a portion of a spinal cord of a patient, a portion of a sympathetic nerve structure of the patient, a portion of a parasympathetic nerve structure of the patient, and/or a portion of a peripheral nerve of the patient.

Though not intended to be bound by theory, in certain circumstances, an epileptic event may be identified at a time before event onset would be determined by electroencephalography, observation by a physician or knowledgeable layman, or both. The time before onset may range from a few seconds up to a few minutes. As such, certain embodiments of the method may be considered to yield a prediction of an epileptic event. It should be noted that the prediction may sometimes be a false positive. However, depending on a physician's judgment, his or her understanding of the devices in use, and the patient's condition, a certain amount of false positives may be tolerable.

Even if no prediction is made, i.e., the methods of various embodiments of this invention are capable of identifying an epileptic event at or after the time of electrographic onset, such information may be useful for identifying an epileptic event without the need for EEG monitoring, implanted sensors, or clinical observation, and with a higher signal-to-noise ratio than EEG monitoring using scalp electrodes. Even though scalp recordings are the most common modality for seizure detection, this modality has low sensitivity (e.g., a large number of epileptic seizures are not accompanied by electrical changes at the scalp), low specificity (e.g., muscle and movement artifacts may resemble electrical seizure activity at the scalp), and also may have long latency between the emergence of epileptic activity in certain brain regions and the appearance, if any, of electrical activity at the scalp.

EEG, implanted sensors, and clinical monitoring or observation often have low signal-to-noise ratios, sensitivity and specificity. These modalities are often disruptive of the patient's normal life, and can generally only be used for limited time periods due to the risk of infection and other injury. These undesirable limitations can generally be avoided in some embodiments of the present method.

Also, the method can make use of multiple modalities of data, thus providing a method of identifying epileptic seizures that may provide greater selectivity, sensitivity, and/or specificity. The information is also useful for identifying an epileptic event with greater accuracy than is generally exhibited by seizure diaries. Surprisingly, seizure diaries kept by the patient are often highly inaccurate with numerous false negatives.

Although not limited to the following, an exemplary system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (e.g., one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979, 511 issued Dec. 25, 1990 to Reese S. Terry, Jr. Lead assembly 122 may be secured, while retaining the ability to flex with movement of the chest and neck, by a suture connection to nearby tissue (not shown).

In alternative embodiments, the electrode assembly 125 may comprise temperature sensing elements, blood pressure sensing elements, and/or heart rate sensor elements. Other sensors for other body parameters may also be employed. Both passive and active stimulation may be combined or delivered by a single IMD according to the present invention. Either or both modes may be appropriate to treat a specific patient under observation.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Figure 2:
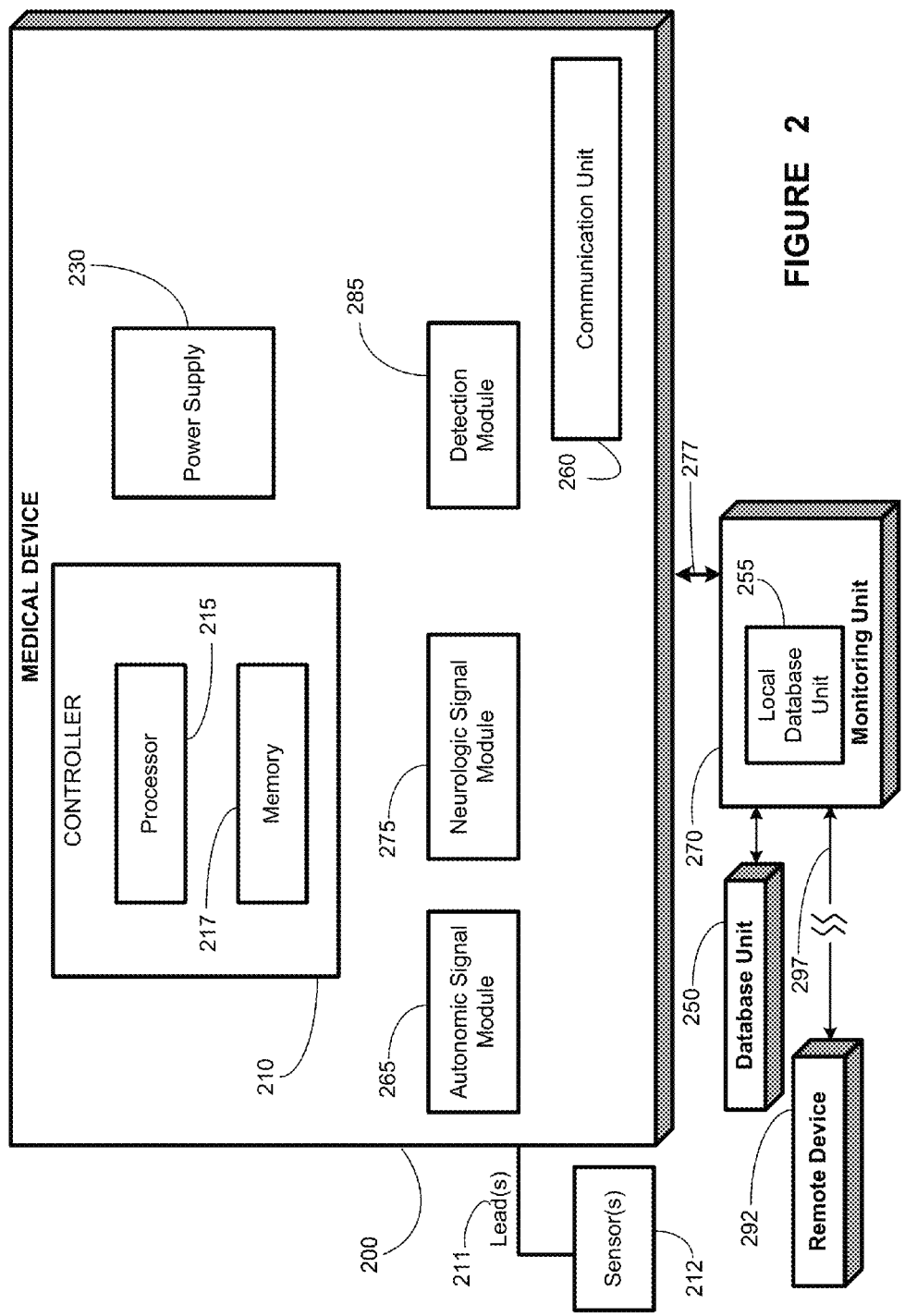
FIG. 2 provides a block diagram of a medical device system that includes a medical device and an external unit, in accordance with one illustrative embodiment of the present invention.

Turning now to FIG. 2, a block diagram depiction of a medical device 200 is provided, in accordance with one illustrative embodiment of the present invention. In some embodiments, the medical device 200 may be implantable (such as implantable electrical signal generator 110 from FIG. 1), while in other embodiments the medical device 200 may be completely external to the body of the patient.

The medical device 200 may comprise a controller 210 capable of controlling various aspects of the operation of the medical device 200. The controller 210 is capable of receiving internal data or external data, and in one embodiment, is capable of causing a stimulation unit (not shown) to generate and deliver an electrical signal, a drug, cooling, or two or more thereof to one or more target tissues of the patient's body for treating a medical condition. For example, the controller 210 may receive manual instructions from an operator externally, or may cause an electrical signal to be generated and delivered based on internal calculations and programming. In other embodiments, the medical device 200 does not comprise a stimulation unit. In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, blood pressure, and/or temperature, and delivering the signals to the medical device 200. The sensor 212 may also be capable of detecting kinetic signal associated with a patient's movement. The sensor 212, in one embodiment, may be an accelerometer. The sensor 212, in another embodiment, may be an inclinometer. In another embodiment, the sensor 212 may be an actigraph. In one embodiment, the sensor(s) 212 may be the same as implanted electrode(s) 126, 128 (FIG. 1). In other embodiments, the sensor(s) 212 are external structures that may be placed on the patient's skin, such as over the patient's heart or elsewhere on the patient's torso. The sensor 212, in one embodiment is a multimodal signal sensor capable of detecting various autonomic and neurologic signals, including kinetic signals associated with the patient's movement.

In one embodiment, the medical device 200 may comprise a autonomic signal module 265 that is capable of collecting autonomic data, e.g., cardiac data comprising fiducial time markers of each of a plurality of heart beats. The autonomic signal module 265 may also process or condition the autonomic data. The autonomic data may be provided by the sensor(s) 212. The autonomic signal module 265 may be capable of performing any necessary or suitable amplifying, filtering, and performing analog-to-digital (A/D) conversions to prepare the signals for downstream processing. The autonomic data module 265, in one embodiment, may comprise software module(s) that are capable of performing various interface functions, filtering functions, etc. In another embodiment, the autonomic signal module 265 may comprise hardware circuitry that is capable of performing these functions. In yet another embodiment, the autonomic signal module 265 may comprise hardware, firmware, software and/or any combination thereof. A more detailed illustration of the autonomic signal module 265 is provided in FIG. 3A and accompanying description below.

The autonomic signal module 265 is capable of collecting autonomic data and providing the collected autonomic data to a detection module 285.

In one embodiment, the medical device 200 may comprise a neurological signal module 275 that is capable of collecting neurologic data, e.g., kinetic signals indicative of the patient's movement. The neurological signal module 275 may also process or condition the neurologic data. The neurologic data may be provided by the sensor(s) 212. The neurological signal module 275 may be capable of performing any necessary or suitable amplifying, filtering, and performing analog-to-digital (A/D) conversions to prepare the signals for downstream processing. The neurological signal module 275, in one embodiment, may comprise software module(s) that are capable of performing various interface functions, filtering functions, etc. In another embodiment, the neurological signal module 275 may comprise hardware circuitry that is capable of performing these functions. In yet another embodiment, the neurological signal module 275 may comprise hardware, firmware, software and/or any combination thereof. Further description of the neurologic signal module 275 is provided in FIG. 3B and accompanying description below.

The neurological signal module 275 is capable of collecting autonomic data and providing the collected autonomic data to a detection module 285.

The detection module 285 is capable of detecting an epileptic event based upon an autonomic signal provided by autonomic signal module 265 and neurological signal module 275. The detection module 285 can implement one or more algorithms using the autonomic data and neurologic data in any particular order, weighting, etc. The detection module 285 may comprise software module(s) that are capable of performing various interface functions, filtering functions, etc. In another embodiment, the detection module 285 may comprise hardware circuitry that is capable of performing these functions. In yet another embodiment, the detection module 285 may comprise hardware, firmware, software and/or any combination thereof. Further description of the detection module 285 is provided in FIG. 3C and accompanying description below.

In addition to components of the medical device 200 described above, a medical device system may comprise a storage unit to store an indication of at least one of seizure or an increased risk of a seizure. The storage unit may be the memory 217 of the medical device 200, another storage unit of the medical device 200, or an external database, such as a local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260. For example, in one embodiment, one or more of the autonomic signal module 265, the neurologic signal module 275, or the detection module 285 may be external to the medical device 200, e.g., in a monitoring unit 270. Locating one or more of the autonomic signal module 265, the neurologic signal module 275, or the detection module 285 outside the medical device 200 may be advantageous if the calculation(s) is/are computationally intensive, in order to reduce energy expenditure and heat generation in the medical device 200 or to expedite calculation.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., wand 155 (FIG. 1) to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting references for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3A:
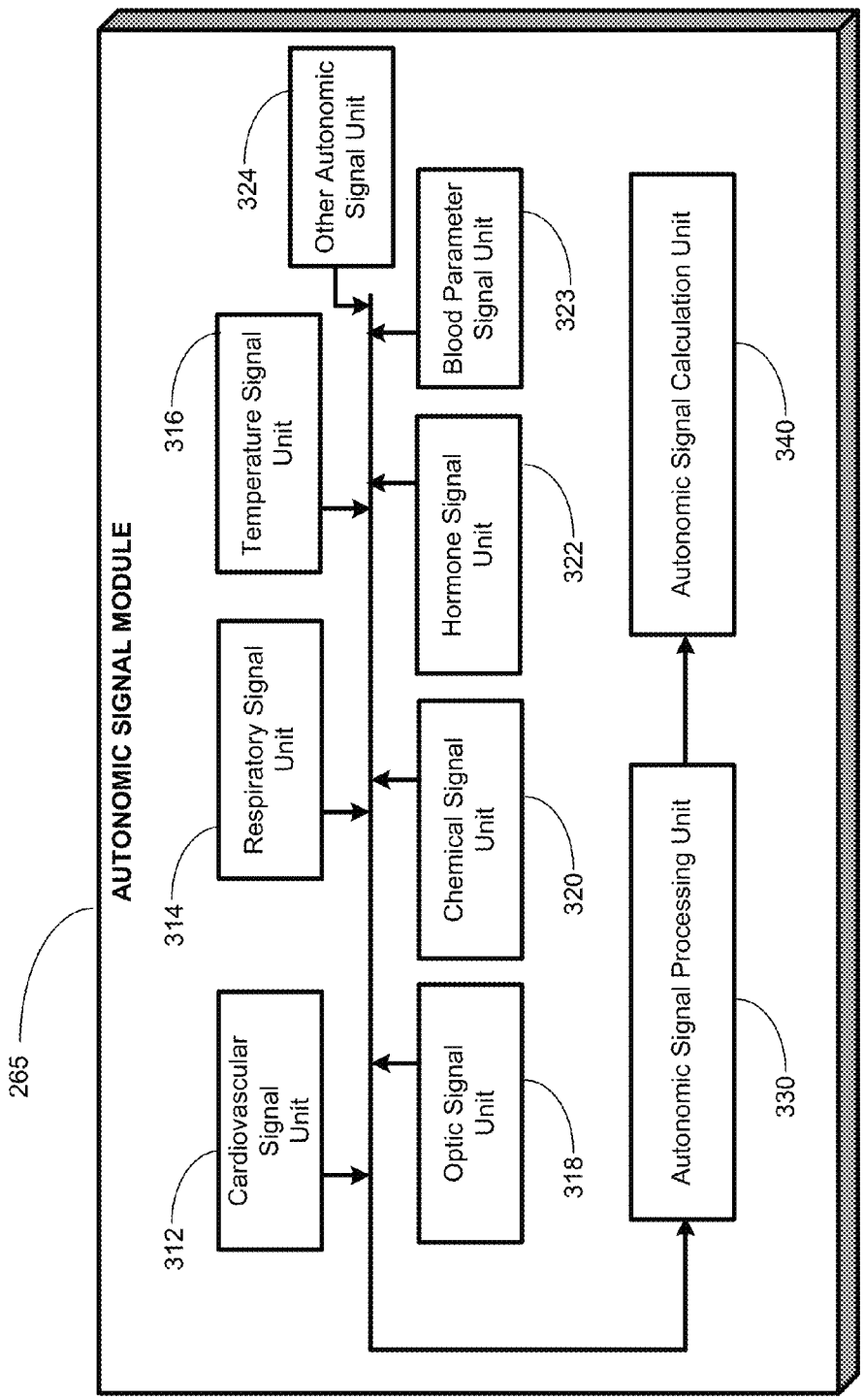
FIG. 3A provides a block diagram of a cardiac signal module of a medical device, in accordance with one illustrative embodiment of the present invention.

Turning to FIG. 3A, an autonomic signal module 265 is shown in more detail. The autonomic signal module 265 can comprise a cardiovascular signal unit 312 capable of providing at least one cardiovascular signal. Alternatively or in addition, the autonomic signal module 265 can comprise a respiratory signal unit 314 capable of providing at least one respiratory signal. Alternatively or in addition, the autonomic signal module 265 can comprise a blood parameter signal unit 323 capable of providing at least one blood parameter signal (e.g., blood glucose, blood pH, blood gas, etc). Alternatively or in addition, the autonomic signal module 265 can comprise a temperature signal unit 316 capable of providing at least one temperature signal. Alternatively or in addition, the autonomic signal module 265 can comprise an optic signal unit 318 capable of providing at least one optic signal. Alternatively or in addition, the autonomic signal module 265 can comprise a chemical signal unit 320 capable of providing at least one body chemical signal. Alternatively or in addition, the autonomic signal module 265 can comprise a hormone signal unit 322 capable of providing at least one hormone signal. Alternatively or in addition, the autonomic signal module 265 can comprise one or more other autonomic signal unit(s) 324, such as a skin resistance signal unit.

The autonomic signal module 265 can also comprise an autonomic signal processing unit 330. The autonomic signal processing unit 330 can perform any filtering, noise reduction, amplification, or other appropriate processing of the data received by the signal units 312-324 desired by the person of ordinary skill in the art prior to calculation of the autonomic signal.

The autonomic signal module 265 can also comprise an autonomic signal calculation unit 340. The autonomic signal calculation unit 340 can calculate an autonomic signal from the data passed by the autonomic signal processing unit 330. A calculated autonomic signal herein refers to any signal derivable from the provided signals, with or without processing by the autonomic signal processing unit 330.

For example, the autonomic signal calculation unit 340 may calculate the heart rate, a change in the heart rate, the speed of change in heart rate, blood pressure, heart sounds, heart rhythm, heartbeat morphology at various scales (see, e.g., U.S. Ser. No. 12/884,051, filed Sep. 16, 2010, and U.S. Ser. No. 12/886,419, filed Sep. 20, 2010, which are hereby incorporated herein by reference), or the shape of the deflection of the thoracic wall as the heart apex beats against it, among others, from cardiovascular data received by cardiovascular signal unit 312.

For another example, the autonomic signal calculation unit 340 may calculate the respiration (breath) rate, respiration pattern, airflow velocity, respiration amplitude (tidal volume, minute volume), arterial gas concentrations such as end-tidal carbon dioxide, among others, from respiratory data received by respiratory signal unit 314.

For still another example, the autonomic signal calculation unit 340 may calculate a change in the skin temperature or skin electrical resistance of a part of the patient's face or a change in the core temperature of the patient, from temperature data received by temperature signal unit 316.

Figure 3B:
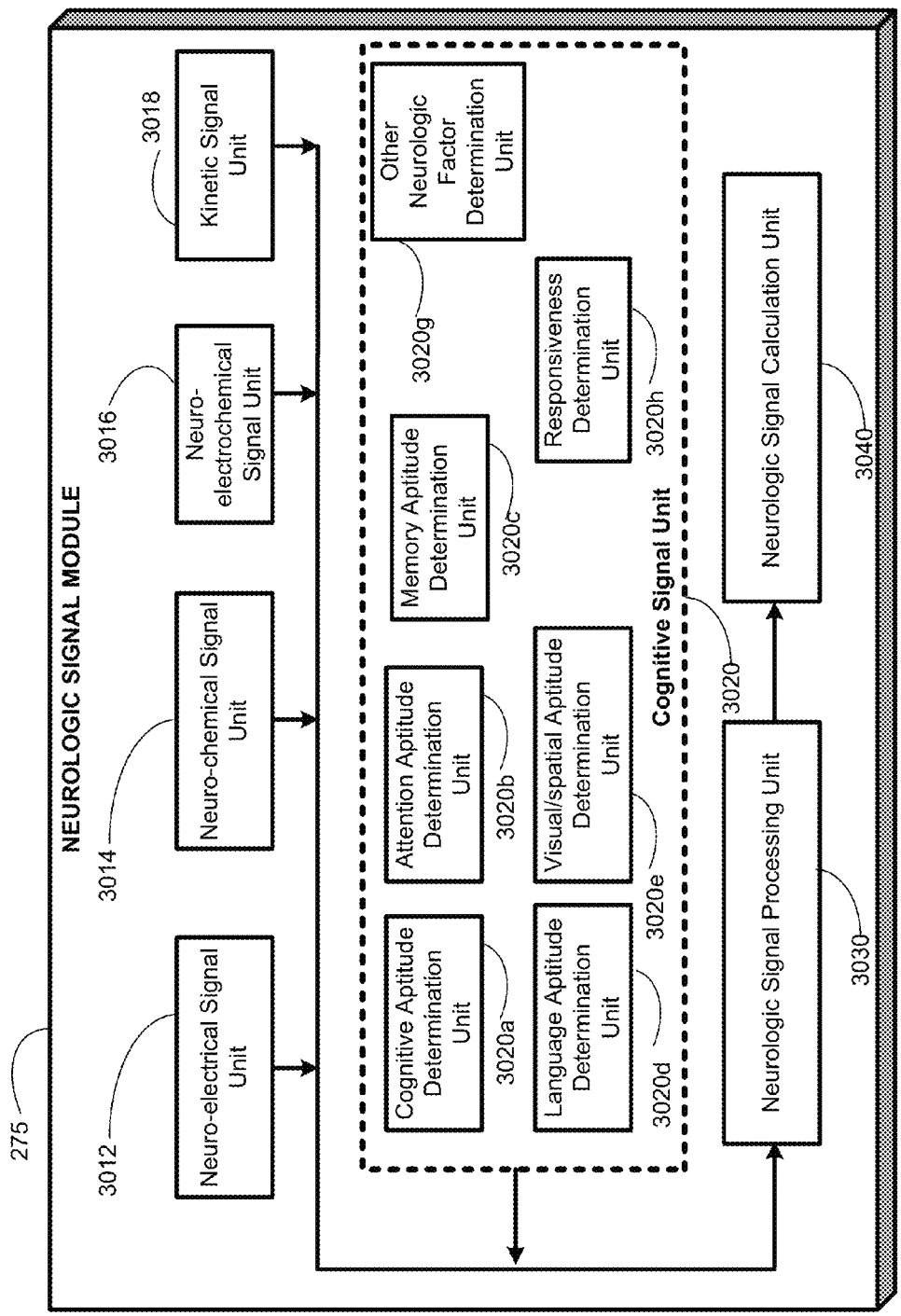
FIG. 3B provides a block diagram of a kinetic signal module of a medical device, in accordance with one illustrative embodiment of the present invention.

Turning to FIG. 3B, an exemplary embodiment of a neurologic signal module 275 is shown. The neurologic signal module 275 can comprise at least one of a neuro-electrical signal unit 3012 capable of providing at least one neuro-electrical signal; a neuro-chemical signal unit 3014 capable of providing at least one neuro-chemical signal; a neuro-electrochemical signal unit 3016 capable of providing at least one neuro-electrochemical signal; a kinetic signal unit 3018 capable of providing at least one kinetic signal; or a cognitive signal unit 3020 capable of providing at least one cognitive signal. The cognitive signal unit 3020 may be a component of a remote device.

In one embodiment, the cognitive signal unit comprises at least one of a cognitive aptitude determination unit 3020a capable of processing at least one cognitive aptitude indication; an attention aptitude determination unit 3020b capable of processing at least one attention aptitude indication; a memory aptitude determination unit 3020c capable of processing at least one memory indication; a language aptitude determination unit 3020d capable of processing at least one language indication; a visual/spatial aptitude determination unit 3020e capable of processing at least one visual/spatial indication; one or more other neurologic factor determination unit(s) 3020g; or a responsiveness determination unit 3020h.

The neurologic signal module 275 can also comprise a neurologic signal processing unit 3030. The neurologic signal processing unit 3030 can perform any filtering, noise reduction, amplification, or other appropriate processing of the data received by the signal units 3012-3020 desired by the person of ordinary skill in the art prior to calculation of the neurologic signal.

The neurologic signal module 275 can also comprise a neurologic signal calculation unit 3040. The neurologic signal calculation unit 3040 can calculate a neurologic signal from the data passed by the neurologic signal processing unit 3030. A calculated neurologic signal herein refers to any signal derivable from the provided signals.

For example, the neurologic signal calculation unit 3040 may calculate a brain activity, such as those determinable from signals yielded by an EEG, ECoG, or depth electrodes (i.e., a deep brain electrode), as received by neuro-electrical signal unit 3012, neuro-chemical signal unit 3014, and/or neuro-electrochemical signal unit 3016 and, optionally, further processed by neurologic data processing unit 3030.

A calculated signal regarding brain activity can also be calculated using other neurological signals. For example, spikes in neurons or axons in the brain and spinal cord including central structures and pathways with autonomic control or modulatory capabilities, cranial nerves (e.g., vagus nerve), autonomic ganglia or nerves and peripheral nerves can be sensed and signals provided. Neural imaging or brain imaging signals may be provided, including, for example: Functional Magnetic Resonance Imaging (fMRI), Magnetoencephalography (MEG), Positron Emission Tomography (PET), Event-Related Optical Signal (EROS), and Diffuse Optical Imaging (DOI)). Other imaging techniques such as voltage-sensitive dyes, ultrasound, infra-red, near infra-red and other forms of thermography may also provide signals from which a brain activity can be calculated.

For another example, the neurologic signal calculation unit 3040 may calculate a body kinetic signal, such as the body's (or of a portion thereof such as the head, an arm, or a leg) acceleration; direction; position; smoothness, amplitude, force of movements and number of movements per unit time, and whether there are extraneous or abnormal body oscillations during resting conditions or movement. The signal may be provided by electromyography, a mechanogram, an accelerometer, an actigraph, and/or an inclinometer, as received by kinetic capability determination unit 3018, and, optionally, further processed by neurologic data processing unit 3030.

Kinetic signals provide insight into the functional state of the nervous system and are thus classified as a neurologic signal. The ability to perform movements: a) in any direction; b) do it smoothly and with precision so that for example, a target (e.g. putting a key into its hole) may be met in the first attempt or handwriting is legible; c) changing direction to avoid colliding with an object interposed on its path to a target and re-adjusting the trajectory to reach the original target; and d) with adaptive force and discriminations so to be able to pick a penny off a flat surface and also lift heavy objects. The acceleration and velocity speed, direction and smoothness may be quantified using tools such as 3-D accelerometers among others.

Figure 3C:
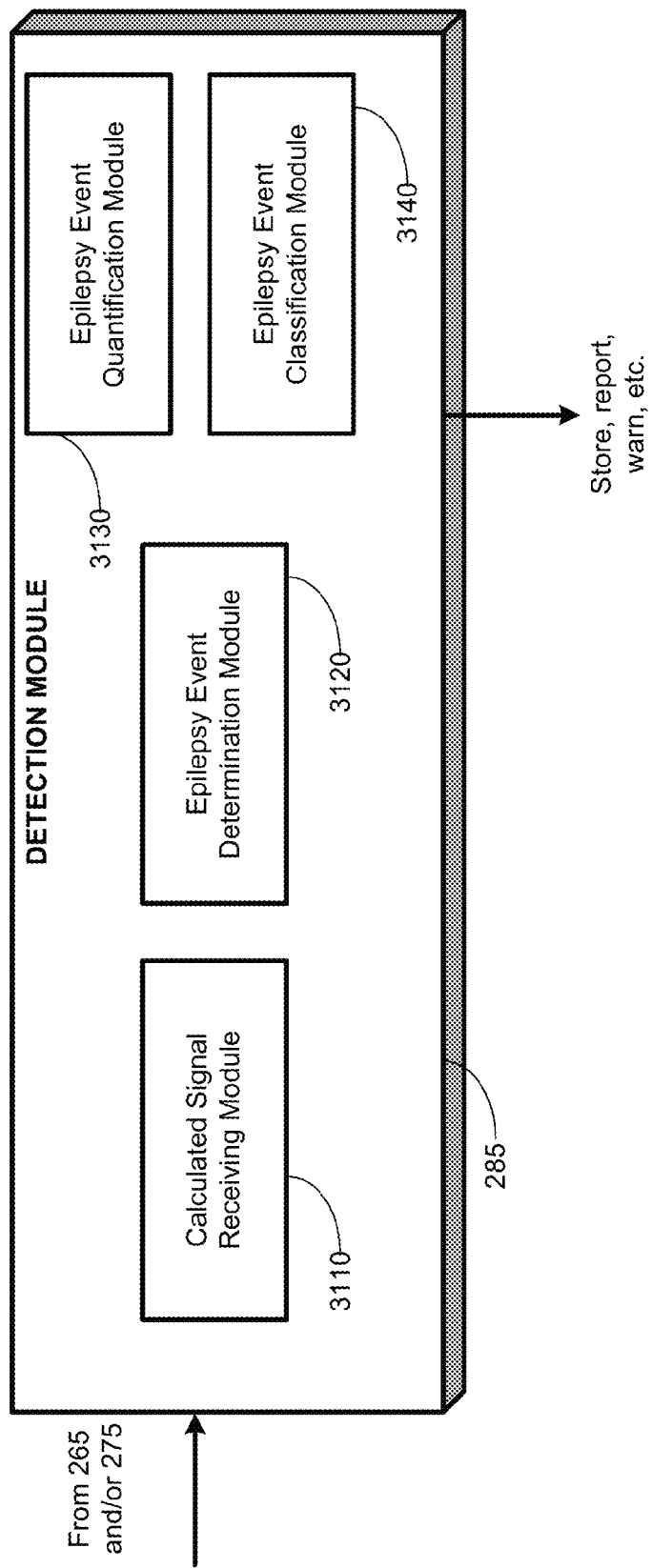
FIG. 3C provides a block diagram of a detection module of a medical device, in accordance with one illustrative embodiment of the present invention.

Turning to FIG. 3C, a block diagram of detection module 285 is depicted. The detection module 285 comprises a calculated signal receiving module 3110 capable of receiving data indicative of a calculated signal from one or more of the autonomic signal module 265 and the neurologic signal module 275 or a memory 217 storing prior outputs of such a module, and epilepsy event determination module 3120 capable of determining from the received data the occurrence of an epileptic event, e.g., a seizure. The epilepsy event determination module 3120 may implement any appropriate algorithms for determining an epilepsy event from autonomic signals and neurologic signals, e.g., from cardiac data and kinetic data, such as those referred to above.

In the embodiment shown in FIG. 3C, the detection module 285 further comprises an epilepsy event quantification module 3130 capable of quantifying from the received data one or more quantifiable characteristics of an epileptic event, e.g., a seizure. Exemplary quantifiable characteristics include, but are not limited to, event duration, duration of stages of the event (e.g., preictal, ictal, and/or postictal stages), values and/or ranges thereof of one or more body signals (e.g., a peak heart rate, a time series of heart rate, etc.), among others.

In the embodiment shown in FIG. 3C, the detection module 285 also comprises an epilepsy event classification module 3140 capable of classifying an epileptic event, e.g., a seizure, e.g., as a partial seizure, a generalized seizure, or an absence seizure; as a simple partial or complex partial seizure; as a primarily generalized seizure or a secondarily generalized seizure, etc. This module may be also used to classify events as epileptic or non-epileptic (e.g., pseudo-seizures, psychogenic seizures, etc.) Although FIG. 3C shows both an epilepsy event quantification module 3130 and an epilepsy event classification module 3140, in other embodiments, either or both of modules 3130-3140 may be omitted.

The detection module 285 may send the output of the epilepsy event determination module 3120 to one or more other modules of the medical device 200 and/or one or more external units. The one or more other modules may then store the output, report the output to the patient, a physician, and/or a caregiver; warn the patient or a caregiver of an epileptic event, etc.

The medical device system of one embodiment of the present invention provides for software module(s) that are capable of acquiring, storing, and processing various forms of data, such as patient data/parameters (e.g., physiological data, side-effects data, heart rate data, breathing rate data, brain-activity parameters, disease progression or regression data, quality of life data, etc.) and therapy parameter data. Therapy parameters may include, but are not limited to, electrical signal parameters (e.g., frequency, pulse width, wave shape, polarity, geometry of electrical fields, on-time, off-time, etc.) that define therapeutic electrical signals delivered by the medical device in response to the detection of the seizure, medication type, dose, or other parameters, and/or any other therapeutic treatment parameter.

In one embodiment, the medical device 200 or an external unit 270 may also be capable of detecting a manual input from the patient. The manual input may include a magnetic signal input, a tap input, a button, dial, or switch input, a touchscreen input, a wireless data input to the medical device 200, etc. The manual input may be used to allow capture of the patient's subjective assessment of his or her epileptic events. For example, the medical device 200 may comprise one or more physical or virtual (e.g., touchscreen-implemented) buttons accessible to the patient's fingers or a caregiver's, through which the patient or caregiver may indicate he or she is having an epileptic event or is not having an epileptic event. Alternatively or in addition, the manual input may be used to gauge the patient's responsiveness.

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

In certain embodiments, the present invention relates to one or more of the following numbered paragraphs:

1. A medical device (implantable or non-implantable) for detecting, quantifying, and/or classifiying an epileptic event based upon an autonomic signal and a neurologic signal of a patient, comprising:
a detection, quantification, and/or classification module(s) for receiving an autonomic signal indicative of the patient's autonomic activity and for receiving a neurologic signal indicative of the patient's neurological activity;
a processing element for determining whether an epileptic event has occurred, a quantifiable characteristic of an epileptic event, and/or a class of an epileptic event, based upon the autonomic signal and the neurologic signal.

2. The implantable medical device of numbered paragraph 1, wherein the autonomic signal is selected from the group consisting of a cardiac signal, a respiratory signal, a skin resistivity signal, a pupillary signal, a blood signal, and two or more thereof.

3. The implantable medical device of numbered paragraph 1, wherein the neurologic signal is selected from the group consisting of a brain signal, a kinetic signal, and two or more thereof.

4. The implantable medical device of numbered paragraph 1, wherein the processing element is further capable of determining whether an epileptic event has occurred, quantifying an epileptic event, or classifying an epileptic event by:
identifying a putative epileptic event, a quantifiable characteristic of an epileptic event, and/or a class of an epileptic event based on one of the autonomic signal and the neurologic signal; and
validating the identifying based on the other of the autonomic signal and the neurologic signal.

101. A method for detecting a generalized tonic-clonic epileptic seizure based upon two or more of a patient's body signals, comprising:
providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; an isometric force signal indicative of the patient's muscle activity; a sound signal indicative of the patient's oral utterances or vocalizations; an ocular signal indicative of the patient's eye movement; a responsiveness signal indicative of the patient's responsiveness; an awareness signal indicative of the patient's awareness; an eye activity signal indicative of the patient's eye activity; and a stress marker signal indicative of at least one stress marker of the patient; and
detecting the generalized tonic-clonic epileptic seizure based upon the timewise correlation of two features, one feature being of each of the at least two body signals, wherein:

the feature of the cardiac signal is an increase in the patient's heart rate above an interictal reference value;
the feature of the accelerometer signal is an increase in the patient's movement above an interictal reference value followed by a decrease in the patient's movement below an interictal reference value;
the feature of the inclinometer signal is a change of the patient's body position indicative of either loss of or increase in postural tone, resulting in a fall;
the feature of the actigraph signal is an increase in the patient's movement above an interictal reference value followed by a decrease in the patient's movement below an interictal reference value, or a change of the patient's body position indicative of a change in body posture including but not limited to a fall;
the feature of the respiratory signal is a respiration rate outside an interictal reference value range;
the feature of the skin resistivity signal is a change in the patient's skin resistivity outside an interictal reference value;
the feature of the blood gas signal is a decrease in the patient's blood oxygen content below an interictal reference value, an increase in carbon dioxide content above an interictal reference value, or both;
the feature of the blood pH signal is a decrease in the patient's blood pH below an interictal reference value;
the feature of the isometric force signal is an increase in the patient's muscle activity above an interictal reference value;
the feature of the sound signal is an increase in the patient's oral utterances or vocalizations indicative of an epileptic cry;
the feature of the ocular signal is a forced eye deviation;
the feature of the responsiveness signal is a decrease in the patient's responsiveness below an interictal reference value;
the feature of the awareness signal is a decrease in the patient's awareness below an interictal reference value;
the feature of the eye signal is a change in one or more of blinking rate, blinking amplitude, and inter-blinking interval outside an interictal reference value range;
and the feature of the stress marker signal is an increase in at least one stress marker of the patient above an interictal reference value.

102. The method of numbered paragraph 101, further comprising:
indicating the end of the generalized tonic-clonic epileptic seizure when each of the features is outside the value or range of values associated with the ictal state for the respective body signal.

103. The method of numbered paragraph 101, further comprising:
indicating the beginning of a post-ictal period based upon the appearance of at least one post-ictal feature of at least one said body signal, wherein:
the post-ictal feature of the cardiac signal is a decrease in the patient's heart rate below an ictal reference value;
the post-ictal feature of the accelerometer signal is a decrease in the patient's movement below an ictal reference value;
the post-ictal feature of the respiratory signal is an increase in the patient's respiration rate above an ictal reference value;
the post-ictal feature of the responsiveness signal is an increase in the patient's responsiveness above an ictal value and below an inter-ictal reference value; and
the post-ictal feature of the awareness signal is an increase in the patient's awareness above an ictal value and below an inter-ictal reference value.

104. The method of numbered paragraph 103, further comprising:
indicating the end of the post-ictal period when each of the post-ictal features is outside the range of values associated with the ictal and post-ictal states.

201. A computer readable program storage device encoded with instructions that, when executed by a computer, performs a method for detecting a partial epileptic seizure based upon two or more of a patient's body signals, comprising:
providing at least two body signals selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; a sound signal indicative of the patient's oral utterances or vocalizations; a responsiveness signal indicative of the patient's responsiveness; an awareness signal indicative of the patient's awareness; an eye activity signal indicative of at least one eye activity of a patient; and a stress marker signal indicative of at least one stress marker of the patient; and
detecting the partial epileptic seizure based upon the timewise correlation of two features, one feature being of each of the at least two body signals, wherein:
the feature of the cardiac signal is a heart rate outside an interictal reference value range;
the feature of the accelerometer signal is a movement outside an interictal reference value range;
the feature of the actigraph signal is a movement outside an interictal reference value range;
the feature of the respiratory signal is a respiration rate outside an interictal reference value range;
the feature of the skin resistivity signal is a skin resistivity outside an interictal reference value;
the feature of the blood gas signal is a blood oxygen content outside an interictal reference value range, a carbon dioxide content outside an interictal reference value range, or both;
the feature of the blood pH signal is a blood pH outside an interictal reference value range;
the feature of the sound signal is an increase or a decrease in the patient's oral utterances or vocalizations above an interictal reference value;
the feature of the eye signal is a change in one or more of blinking rate, blinking amplitude, and inter-blinking interval outside an interictal reference value range;
and the feature of the stress marker signal is a concentration of at least one stress marker of the patient above an interictal reference value.

202. The computer readable program storage device encoded with instructions that, when executed by a computer, perform the method of numbered paragraph 201, wherein the method further comprises:
classifying the partial epileptic seizure as a complex partial seizure if a feature of the signal timewise correlated with the at least two body signals and/or a feature of the awareness signal timewise correlated with the at least two body signals is a decrease in the patient's responsiveness below its reference value and/or awareness below its reference value, and as a simple partial seizure if there is no decrease in the patient's responsiveness below its reference value and no decrease in the patient's awareness below its reference value or, if there is a decrease in the patient's responsiveness but awareness remains preserved.

203. The computer readable program storage device encoded with instructions that, when executed by a computer, perform the method of numbered paragraph 201, wherein the method further comprising:
indicating the end of the partial epileptic seizure when each of the features of the respective body signals is outside the range of values associated with the ictal state for that body signal.

204. The computer readable program storage device encoded with instructions that, when executed by a computer, perform the method of numbered paragraph 201, wherein the method further comprising:
indicating the beginning of a post-ictal period when each of the respective body signals is outside the range of values associated with the ictal and inter-ictal states for that body signal, wherein:
the cardiac signal outside the range of values associated with the ictal state;
the post-ictal feature of the accelerometer signal is a change in the patient's movement outside the ictal range of values;
the post-ictal feature of the respiratory signal is a change in the patient's respiration to a value outside an ictal reference value;
the post-ictal feature of the responsiveness signal is an increase in the patient's responsiveness above an ictal reference value but remaining below and inter-ictal reference value; and
the post-ictal feature of the awareness signal is an increase in the patient's awareness above an ictal reference value but remaining below an inter-ictal reference value.

205. The computer readable program storage device encoded with instructions that, when executed by a computer, perform the method of numbered paragraph 204, wherein the method further comprises:
indicating the end of the post-ictal period when each of the features is absent from its respective body signal.

301. A medical device system for detecting an epileptic event based upon multimodal signals, comprising:
a first sensor for detecting a first modal data and a second sensor for detecting a second modal data relating to a patient's body, the first modal data comprising a neurologic signal and the second modal data comprising an autonomic signal of the patient's body; and
an implantable medical device (IMD) operatively coupled to the first sensor and the second sensor; the IMD comprising:
a neurologic signal module for receiving the neurologic signal;
an autonomic signal module for receiving the autonomic signal; and
a processing element for determining whether an epileptic event has occurred based upon the first and second modal data.

401. A method for detecting, quantifying, and/or classifying an epileptic event based upon two or more of a patient's body signals, comprising:
providing at least one body signal selected from the group consisting of a cardiac signal indicative of the patient's heart beats; an accelerometer signal indicative of the patient's movement; an inclinometer signal indicative of the patient's body position; an actigraph signal indicative of the patient's movement, body position, or both; a respiratory signal indicative of the patient's respiration; a skin resistivity signal indicative of the patient's skin resistivity; an blood gas signal indicative of the patient's blood oxygen content, carbon dioxide content, or both; a blood pH signal indicative of the patient's blood pH; an isometric force signal indicative of the patient's muscle activity; a sound signal indicative of the patient's oral utterances or vocalizations; an ocular signal indicative of the patient's eye movement; a responsiveness signal indicative of the patient's responsiveness; an awareness signal indicative of the patient's awareness; and a stress marker signal indicative of at least one stress marker of the patient;
detecting a transition from a preictal time period to an ictal time period using at least a first body signal;
detecting a transition from a preictal time period to an ictal time period using at least a second body signal;
detecting a transition from an ictal time period to a postictal time period using at least a third body signal; and
detecting a transition from a postictal time period to an inter-ictal time period using at least a fourth body signal.

402. The method of numbered paragraph 401, wherein the first body signal, the second body signal, the third, body signal and the fourth body signal are selected from at least two provided body signals.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A medical device system for detecting an epileptic event based upon a patient's cardiac signal and kinetic activity, comprising:
a first sensor for detecting a cardiac signal indicative of a patient's heart activity;
a second sensor for detecting a kinetic signal indicative of body movement of the patient; and
a medical device (MD) coupled to the patient's body and operatively coupled to the first sensor and the second sensor; the MD comprising:
a kinetic signal module for receiving the kinetic signal;
a cardiac signal module for receiving the cardiac signal;
a cardiac index module for determining at least one cardiac index from the cardiac signal, wherein said at least one cardiac index is selected from a heart rate, a heart rhythm, an EKG morphology feature, or an EKG wave interval;
a detection module for determining whether an epileptic event has occurred based on a change in the at least one cardiac index, wherein said change in said at least one cardiac index is selected from an increase in the patient's heart rate; a decrease in the patient's heart rate; or a change in said at least one heart rhythm, EKG morphology feature, or EKG wave interval; and
an action module for taking a further action based on said kinetic signal, wherein the further action is selected from confirming the detecting of the epileptic event, or not confirming the detecting of the epileptic event.

2. The medical device system of claim 1, further comprising:
a kinetic index module for determining at least one kinetic index from the kinetic signal, wherein the kinetic index is selected from:
a body posture,
a body position,
a fall,
a cessation of movement, a parameter derived from an accelerometer signal selected from a movement, a frequency per unit time, a time interval between movements, a movement direction in at least one plane, an acceleration, a velocity, a force,
a parameter derived from an inclinometer signal, or
a change in one or more of the foregoing,
wherein said action module takes said further action based on the at least one kinetic index.

3. The medical device system of claim 1, wherein said action module takes said further action based upon a temporal relationship between a change in the at least one cardiac index and the kinetic signal.

4. The medical device system of claim 1, further comprising a classification module for classifying said epileptic event based upon at least one of said cardiac index, a kinetic index, a respiratory index, a skin index, a blood gases signal, a blood pH, a force index, vocal sounds, ocular activity, an EEG signal, an ECoG signal, an EMG signal, a responsiveness of the patient, an awareness of the patient, or a stress marker.

5. The medical device system of claim 4, wherein said classification module is configured to classify the event as one or more of:
an unconfirmed seizure;
a confirmed seizure;
a non-epileptic seizure;
a primarily generalized tonic-clonic seizure,
a secondarily generalized tonic-clonic seizure;
an absence seizure;
a partial seizure;
a simple partial seizure;
a complex partial seizure;
a simple partial seizure with secondary generalization; or
a complex partial seizure with secondary generalization.

6. The medical device system of claim 4, wherein said classification module is configured to classify the event as one or more of:
a generalized seizure;
a partial seizure;
an absence seizure; or
a non-epileptic seizure.

7. The medical device system of claim 4, further comprising at least one of
a responsiveness module for providing a signal indicative of the patient's responsiveness following said confirming of said epileptic event, and
an awareness module for providing a signal indicative of the patient's awareness following said confirming of said epileptic event,
wherein the classification module is configured to classify the epileptic event based upon the at least one of the responsiveness signal and the awareness signal.

8. The medical device system of claim 1, wherein said action module is configured to not confirm said detecting of said epileptic event by overriding said detecting.

9. A medical device system for detecting an epileptic event based upon a patient's cardiac signal and kinetic activity, comprising:
a first sensor for detecting a cardiac signal indicative of a patient's heart activity;
a second sensor for detecting a kinetic signal indicative of body movement of the patient; and
a medical device (MD) coupled to the patient's body and operatively coupled to the first sensor and the second sensor; the MD comprising:
a kinetic signal module for receiving the kinetic signal;
a cardiac signal module for receiving the cardiac signal;
a kinetic index module for determining at least one kinetic index from the kinetic signal, wherein said at least one kinetic index is selected from a body posture, a body position, a fall, a parameter derived from an accelerometer signal selected from a movement, a frequency per unit time, a time interval between movements, a movement direction in at least one plane, an acceleration, a velocity, a force, a parameter derived from an inclinometer signal, or a change in one or more of the foregoing;
a detection module for determining whether an epileptic event has occurred based on a change in the at least one kinetic index; and
an action module for taking a further action based on said cardiac signal, wherein the further action is selected from confirming the detecting of the epileptic event, or not confirming the detecting of the epileptic event.

10. The medical device system of claim 9, further comprising:
a cardiac index module for determining at least one cardiac index selected from a heart rate, an EKG morphology feature, a heart rhythm, or an EKG wave interval feature,
wherein said action module takes said further action based on the at least one cardiac index.

11. The medical device system of claim 9, wherein said action module takes said further action based upon a temporal relationship between a change in the at least one cardiac index and the kinetic signal.

12. The medical device system of claim 9, further comprising a classification module for classifying said epileptic event based upon at least one of said kinetic index, a cardiac index, a respiratory index, a skin index, a blood gases signal, a blood pH, a force index, vocal sounds, ocular activity, an EEG signal, an ECoG signal, an EMG signal, a responsiveness of the patient, an awareness of the patient, or a stress marker.

13. The medical device system of claim 12, wherein said classification module is configured to classify said event comprises classifying the event as one or more of:
an unconfirmed seizure;
a confirmed seizure;
a non-epileptic seizure;
a primarily generalized tonic-clonic seizure,
a secondarily generalized tonic-clonic seizure;
an absence seizure;
a partial seizure;
a simple partial seizure;
a complex partial seizure;
a simple partial seizure with secondary generalization; or
a complex partial seizure with secondary generalization.

14. The medical device system of claim 12, wherein said classification module is configured to classify the event as one or more of:
a generalized seizure;
a partial seizure;
an absence seizure; or
a non-epileptic seizure.

15. The medical device system of claim 11, further comprising at least one of
a responsiveness module for providing a signal indicative of the patient's responsiveness following said confirming of said epileptic event, and
an awareness module for providing a signal indicative of the patient's awareness following said confirming of said epileptic event, wherein the classification module is configured to classify the epileptic event based upon the at least one of the responsiveness signal and the awareness signal.

16. The medical device system of claim 9, wherein said action module is configured to not confirm said detecting of said epileptic event by overriding said detecting.

17. A medical device system for detecting an epileptic event based upon a patient's cardiac signal and kinetic activity, comprising:
a first sensor for detecting a cardiac signal indicative of a patient's heart activity;
a second sensor for detecting a kinetic signal indicative of body movement of the patient; and
a medical device (MD) coupled to the patient's body and operatively coupled to the first sensor and the second sensor; the MD comprising:
a kinetic signal module for receiving the kinetic signal;
a cardiac signal module for receiving the cardiac signal;
a cardiac index module for determining at least one cardiac index from the cardiac signal, wherein said at least one cardiac index is selected from a heart rate, a heart rhythm, an EKG morphology feature, or an EKG wave interval;
a first characterization module for characterizing the at least one cardiac index as either indicative of an epileptic event or not indicative of an epileptic event;
a kinetic index module for determining at least one kinetic index from the kinetic signal, wherein said at least one kinetic index is selected from a body posture, a body position, a fall, a parameter derived from an accelerometer signal selected from a movement, a frequency per unit time, a time interval between movements, a movement direction in at least one plane, an acceleration, a velocity, a force, a parameter derived from an inclinometer signal, or a change in one or more of the foregoing;
a second characterization module for characterizing the kinetic signal as either indicative of an epileptic event or not indicative of an epileptic event; and
an epileptic event detection module for detecting an epileptic event based on both the cardiac signal and the kinetic signal being indicative of the epileptic event.

18. The medical device system of claim 17, further comprising a module for taking a further action in response to detecting an epileptic event, wherein said further action is selected from providing a therapy to the patient, providing a warning to one of a patient or a caregiver, or logging data relating to the epileptic event.

19. The medical device system of claim 17, wherein the cardiac signal module is an electrocardiogram (EKG), and the kinetic signal module is an accelerometer, an inclinometer, an actigraph, an EMG, a mechanogram, or two or more thereof.

20. The medical device system of claim 17, further comprising a classification module for classifying said epileptic event based upon at least one cardiac index and at least one kinetic index.

21. The medical device system of claim 20, wherein said classification module is configured to classify said epileptic event as one or more of:
an unconfirmed seizure;
a confirmed seizure;
a non-epileptic seizure;
a primarily generalized tonic-clonic seizure,
a secondarily generalized tonic-clonic seizure;
an absence seizure;
a partial seizure;
a simple partial seizure;
a complex partial seizure;
a simple partial seizure with secondary generalization;
a complex partial seizure with secondary generalization.

22. The medical device system of claim 20, wherein said classification module is configured to classify the epileptic event as one or more of:
a generalized seizure;
a partial seizure;
an absence seizure; or
a non-epileptic seizure.

23. The medical device system of claim 20, further comprising at least one of
a responsiveness module for providing a signal indicative of the patient's responsiveness following said confirming of said epileptic event, and
an awareness module for providing a signal indicative of the patient's awareness following said confirming of said epileptic event,
wherein the classification module is configured to classify the epileptic event based upon the at least one of the responsiveness signal and the awareness signal.

* * * * *